(12) United States Patent
Kelbie et al.

(10) Patent No.: US 12,083,263 B2
(45) Date of Patent: Sep. 10, 2024

(54) NEGATIVE PRESSURE WOUND TREATMENT APPARATUSES AND METHODS WITH INTEGRATED ELECTRONICS

(71) Applicant: Smith & Nephew PLC, Watford (GB)

(72) Inventors: William Kelbie, Inverness (GB); Daniel Lee Steward, Kingston upon Hull (GB)

(73) Assignee: Smith & Nephew PLC, Watford (GB)

(*) Notice: Subject to any disclaimer, the term of this patent is extended or adjusted under 35 U.S.C. 154(b) by 348 days.

(21) Appl. No.: 17/439,715

(22) PCT Filed: Mar. 18, 2020

(86) PCT No.: PCT/EP2020/057407
§ 371 (c)(1),
(2) Date: Sep. 15, 2021

(87) PCT Pub. No.: WO2020/187971
PCT Pub. Date: Sep. 24, 2020

(65) Prior Publication Data
US 2022/0160952 A1    May 26, 2022

(30) Foreign Application Priority Data
Mar. 20, 2019  (GB) ..................... 1903774

(51) Int. Cl.
*A61M 1/00*     (2006.01)
*A61F 13/05*    (2024.01)
(52) U.S. Cl.
CPC ............. *A61M 1/962* (2021.05); *A61F 13/05* (2024.01); *A61M 2205/7518* (2013.01)

(58) Field of Classification Search
CPC ........ A61M 35/00; A61M 1/00; A61M 1/962; A61M 2205/7518; A61M 1/915;
(Continued)

(56) References Cited

U.S. PATENT DOCUMENTS

| | | |
|---|---|---|
| 3,874,387 A | 4/1975 | Barbieri |
| 4,224,941 A | 9/1980 | Stivala |

(Continued)

FOREIGN PATENT DOCUMENTS

| | | |
|---|---|---|
| CN | 101744688 A | 6/2010 |
| CN | 201664463 U | 12/2010 |

(Continued)

OTHER PUBLICATIONS

International Search Report and Written Opinion for Application No. PCT/EP2020/057407, mailed on May 12, 2020, 11 pages.

(Continued)

*Primary Examiner* — Adam Marcetich
(74) *Attorney, Agent, or Firm* — Knobbe, Martens, Olson & Bear, LLP

(57) ABSTRACT

Disclosed herein are embodiments of a wound treatment apparatus with electronic components integrated within a wound dressing. In some embodiments, a wound dressing apparatus can comprise a wound dressing. The wound dressing can comprise an absorbent material, an electronics unit comprising a negative pressure source, the electronics unit integrated within the wound dressing and at least partially encapsulated by a preshaped film material or film. The preshaped film material can be incorporated into the wound dressing and can comprise an aperture configured to permit fluid communication between the absorbent material and the negative pressure source.

16 Claims, 30 Drawing Sheets

(58) Field of Classification Search
CPC .. A61M 2205/3306; A61M 2205/3344; A61M 2205/3368; A61M 2205/583; A61M 1/964; A61M 1/966; A61M 2205/8206; A61M 1/90; A61M 1/985; A61M 27/00; A61M 2205/82; A61M 2207/00; A61F 13/00; A61F 13/02; A61F 13/00068; A61F 13/0216; A61F 13/022; A61F 13/05; A61F 2013/00174; A61F 13/023; A61F 2013/00553; A61F 2013/0057; A61F 2013/0091; A61F 2013/00536

See application file for complete search history.

(56) References Cited

U.S. PATENT DOCUMENTS

| | | | |
|---|---|---|---|
| 4,398,910 A | 8/1983 | Blake et al. | |
| 4,534,356 A | 8/1985 | Papadakis | |
| 4,569,674 A | 2/1986 | Phillips et al. | |
| 4,624,656 A | 11/1986 | Clark et al. | |
| 4,681,562 A | 7/1987 | Beck et al. | |
| 4,767,943 A | 8/1988 | Adler et al. | |
| 4,979,944 A | 12/1990 | Luzsicza | |
| 5,055,195 A | 10/1991 | Trasch et al. | |
| 5,055,198 A | 10/1991 | Shettigar | |
| 5,056,510 A | 10/1991 | Gilman | |
| 5,152,757 A | 10/1992 | Eriksson | |
| 5,181,905 A | 1/1993 | Flam | |
| 5,266,928 A | 11/1993 | Johnson | |
| D357,743 S | 4/1995 | Bilitz et al. | |
| 5,527,293 A | 6/1996 | Zamierowski | |
| 5,549,584 A | 8/1996 | Gross | |
| 5,636,643 A | 6/1997 | Argenta et al. | |
| 5,643,189 A | 7/1997 | Masini | |
| 5,779,657 A | 7/1998 | Daneshvar | |
| 5,833,646 A | 11/1998 | Masini | |
| 5,902,256 A | 5/1999 | Benaron | |
| 5,964,723 A | 10/1999 | Augustine | |
| 6,071,267 A | 6/2000 | Zamierowski | |
| 6,142,982 A | 11/2000 | Hunt et al. | |
| 6,168,800 B1 | 1/2001 | Dobos et al. | |
| 6,183,438 B1 | 2/2001 | Berguer | |
| 6,225,523 B1 | 5/2001 | Masini | |
| 6,261,276 B1 | 7/2001 | Reitsma | |
| 6,261,283 B1 | 7/2001 | Morgan et al. | |
| 6,398,767 B1 | 6/2002 | Fleischmann | |
| 6,458,109 B1 | 10/2002 | Henley et al. | |
| 6,471,982 B1 | 10/2002 | Lydon et al. | |
| 6,506,184 B1 * | 1/2003 | Villefrance | A61F 5/441 604/333 |
| 6,599,262 B1 | 7/2003 | Masini | |
| 6,607,495 B1 | 8/2003 | Skalak et al. | |
| 6,685,681 B2 | 2/2004 | Lockwood et al. | |
| 6,787,682 B2 | 9/2004 | Gilman | |
| 6,794,554 B2 | 9/2004 | Sessions et al. | |
| 6,800,074 B2 | 10/2004 | Henley et al. | |
| 6,855,135 B2 | 2/2005 | Lockwood et al. | |
| 6,942,633 B2 | 9/2005 | Odland | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,022,113 B2 | 4/2006 | Lockwood et al. | |
| 7,067,709 B2 | 6/2006 | Murata et al. | |
| 7,070,584 B2 | 7/2006 | Johnson et al. | |
| 7,087,806 B2 | 8/2006 | Scheinberg et al. | |
| 7,108,683 B2 | 9/2006 | Zamierowski | |
| 7,338,482 B2 | 3/2008 | Lockwood et al. | |
| 7,361,184 B2 | 4/2008 | Joshi | |
| 7,524,315 B2 | 4/2009 | Blott et al. | |
| 7,553,306 B1 | 6/2009 | Hunt et al. | |
| 7,569,742 B2 | 8/2009 | Haggstrom et al. | |
| 7,611,500 B1 | 11/2009 | Lina et al. | |
| 7,615,036 B2 | 11/2009 | Joshi et al. | |
| D605,775 S | 12/2009 | Koch et al. | |
| D608,007 S | 1/2010 | Arbesman et al. | |
| 7,645,253 B2 | 1/2010 | Gura et al. | |
| 7,687,678 B2 | 3/2010 | Jacobs | |
| 7,699,823 B2 | 4/2010 | Haggstrom et al. | |
| 7,776,028 B2 | 8/2010 | Miller et al. | |
| 7,779,625 B2 | 8/2010 | Joshi et al. | |
| D625,422 S | 10/2010 | Arbesman et al. | |
| 7,815,616 B2 | 10/2010 | Boehringer et al. | |
| 7,837,673 B2 | 11/2010 | Vogel | |
| 7,846,141 B2 | 12/2010 | Weston | |
| 7,896,864 B2 | 3/2011 | Lockwood et al. | |
| 7,922,676 B2 | 4/2011 | Daskal et al. | |
| 7,922,703 B2 | 4/2011 | Riesinger | |
| 7,942,866 B2 | 5/2011 | Radl et al. | |
| 7,959,624 B2 | 6/2011 | Riesinger | |
| 7,976,519 B2 | 7/2011 | Bubb et al. | |
| 8,007,257 B2 | 8/2011 | Heaton et al. | |
| 8,007,481 B2 | 8/2011 | Schuessler et al. | |
| 8,062,272 B2 | 11/2011 | Weston | |
| 8,080,702 B2 | 12/2011 | Blott et al. | |
| 8,092,441 B2 | 1/2012 | Sugito | |
| 8,158,844 B2 | 4/2012 | McNeil | |
| 8,167,869 B2 | 5/2012 | Wudyka | |
| 8,212,100 B2 | 7/2012 | Moore | |
| 8,215,929 B2 | 7/2012 | Shen et al. | |
| 8,323,264 B2 | 12/2012 | Weston et al. | |
| 8,371,829 B2 | 2/2013 | Jaeb et al. | |
| 8,372,049 B2 | 2/2013 | Jaeb et al. | |
| 8,372,050 B2 | 2/2013 | Jaeb et al. | |
| 8,404,921 B2 | 3/2013 | Lee et al. | |
| 8,409,160 B2 | 4/2013 | Locke et al. | |
| 8,414,519 B2 | 4/2013 | Hudspeth et al. | |
| 8,419,696 B2 | 4/2013 | Wilkes | |
| 8,425,478 B2 | 4/2013 | Olson | |
| 8,439,894 B1 | 5/2013 | Miller | |
| 8,449,508 B2 | 5/2013 | Coulthard et al. | |
| 8,500,776 B2 | 8/2013 | Ebner | |
| 8,529,548 B2 | 9/2013 | Blott et al. | |
| 8,545,466 B2 | 10/2013 | Andresen et al. | |
| 8,579,872 B2 | 11/2013 | Coulthard et al. | |
| 8,603,074 B2 | 12/2013 | Kagan | |
| 8,604,265 B2 | 12/2013 | Locke et al. | |
| 8,641,691 B2 | 2/2014 | Fink et al. | |
| 8,641,693 B2 | 2/2014 | Locke et al. | |
| 8,702,665 B2 | 4/2014 | Locke et al. | |
| 8,764,732 B2 | 7/2014 | Hartwell | |
| 8,795,257 B2 | 8/2014 | Coulthard et al. | |
| 8,808,274 B2 | 8/2014 | Hartwell | |
| 8,814,842 B2 | 8/2014 | Coulthard et al. | |
| 8,821,458 B2 | 9/2014 | Locke et al. | |
| 8,829,263 B2 * | 9/2014 | Haggstrom | A61F 13/00068 602/53 |
| 8,870,837 B2 | 10/2014 | Locke et al. | |
| 8,961,496 B2 | 2/2015 | Locke et al. | |
| 8,974,429 B2 | 3/2015 | Gordon et al. | |
| 9,061,095 B2 | 6/2015 | Adie et al. | |
| 9,084,845 B2 | 7/2015 | Adie et al. | |
| 9,089,630 B2 | 7/2015 | Perkins et al. | |
| 9,198,802 B2 | 12/2015 | Robinson et al. | |
| 9,259,558 B2 | 2/2016 | Tsai | |
| 9,265,665 B2 | 2/2016 | Robinson et al. | |
| 9,283,118 B2 | 3/2016 | Locke et al. | |
| 9,393,354 B2 | 7/2016 | Freedman et al. | |
| 9,414,968 B2 | 8/2016 | Heagle | |
| 9,421,133 B2 | 8/2016 | Hu et al. | |
| 9,427,505 B2 | 8/2016 | Askem et al. | |
| 9,452,088 B2 | 9/2016 | Shulman et al. | |
| 9,560,975 B2 | 2/2017 | Mei et al. | |
| D787,690 S | 5/2017 | MacKay et al. | |
| 9,737,649 B2 | 8/2017 | Begin et al. | |
| 9,770,368 B2 | 9/2017 | Robinson et al. | |
| 9,814,811 B2 | 11/2017 | Aalders et al. | |
| 9,907,703 B2 | 3/2018 | Allen et al. | |
| 9,925,092 B2 | 3/2018 | Luckemeyer et al. | |
| RE46,778 E | 4/2018 | Peron | |
| 9,956,120 B2 | 5/2018 | Locke | |
| 10,004,914 B2 | 6/2018 | Nettesheim et al. | |
| 10,016,544 B2 | 7/2018 | Coulthard et al. | |
| 10,046,095 B1 | 8/2018 | Middaugh et al. | |
| 10,046,096 B2 | 8/2018 | Askem et al. | |

(56) References Cited

U.S. PATENT DOCUMENTS

| | | | |
|---|---|---|---|
| 10,086,117 B2 | 10/2018 | Locke et al. | |
| 2003/0212357 A1 | 11/2003 | Pace | |
| 2004/0076662 A1 | 4/2004 | Riesinger | |
| 2004/0087884 A1 | 5/2004 | Haddock et al. | |
| 2004/0167482 A1 | 8/2004 | Watson | |
| 2005/0012616 A1 | 1/2005 | Forster et al. | |
| 2005/0045461 A1 | 3/2005 | Sweetland et al. | |
| 2005/0065471 A1 | 3/2005 | Kuntz | |
| 2005/0119737 A1 | 6/2005 | Bene et al. | |
| 2005/0137539 A1 | 6/2005 | Biggie et al. | |
| 2006/0029650 A1 | 2/2006 | Coffey | |
| 2006/0086598 A1 | 4/2006 | Sneek et al. | |
| 2006/0107642 A1 | 5/2006 | Smith et al. | |
| 2006/0259102 A1 | 11/2006 | Slatkine | |
| 2007/0055209 A1 | 3/2007 | Patel et al. | |
| 2007/0128055 A1 | 6/2007 | Lee | |
| 2007/0179460 A1 | 8/2007 | Adahan | |
| 2007/0225663 A1 | 9/2007 | Watt et al. | |
| 2007/0255187 A1 | 11/2007 | Branch | |
| 2007/0265585 A1* | 11/2007 | Joshi | A61M 1/962 604/313 |
| 2007/0265586 A1* | 11/2007 | Joshi | A61M 1/78 604/313 |
| 2008/0021356 A1 | 1/2008 | Escude et al. | |
| 2008/0051716 A1 | 2/2008 | Stutz | |
| 2009/0012484 A1 | 1/2009 | Nielsen et al. | |
| 2009/0048556 A1 | 2/2009 | Durand | |
| 2010/0022990 A1 | 1/2010 | Karpowicz et al. | |
| 2010/0100160 A1 | 4/2010 | Edman et al. | |
| 2010/0137775 A1 | 6/2010 | Hu et al. | |
| 2010/0160881 A1 | 6/2010 | Lin et al. | |
| 2010/0280469 A1 | 11/2010 | Hall et al. | |
| 2010/0292632 A1 | 11/2010 | Mulvihill et al. | |
| 2011/0028918 A1* | 2/2011 | Hartwell | A61F 13/0226 604/319 |
| 2011/0054421 A1* | 3/2011 | Hartwell | A61M 1/964 604/319 |
| 2011/0092927 A1 | 4/2011 | Wilkes et al. | |
| 2011/0112492 A1 | 5/2011 | Bharti et al. | |
| 2011/0224631 A1 | 9/2011 | Simmons et al. | |
| 2011/0292623 A1 | 12/2011 | Stanley | |
| 2011/0305736 A1 | 12/2011 | Wieland et al. | |
| 2012/0016323 A1* | 1/2012 | Robinson | A61M 1/982 604/319 |
| 2012/0059294 A1 | 3/2012 | Schubert et al. | |
| 2012/0109034 A1 | 5/2012 | Locke et al. | |
| 2013/0090616 A1* | 4/2013 | Neubauer | A61F 13/02 604/319 |
| 2013/0215638 A1 | 8/2013 | Dabov et al. | |
| 2014/0100536 A1 | 4/2014 | Angel | |
| 2014/0343518 A1 | 11/2014 | Riesinger | |
| 2015/0057625 A1 | 2/2015 | Coulthard | |
| 2015/0174304 A1* | 6/2015 | Askem | A61F 13/0246 604/319 |
| 2015/0202354 A1 | 7/2015 | Wall | |
| 2016/0015873 A1 | 1/2016 | Robinson et al. | |
| 2016/0166438 A1 | 6/2016 | Rovaniemi | |
| 2016/0199546 A1 | 7/2016 | Chao | |
| 2016/0242964 A1 | 8/2016 | Rapp et al. | |
| 2016/0271305 A1 | 9/2016 | Kurihara et al. | |
| 2016/0361473 A1 | 12/2016 | Robinson et al. | |
| 2017/0112974 A1 | 4/2017 | Fujisaki | |
| 2017/0112975 A1 | 4/2017 | Fujisaki | |
| 2017/0127525 A1 | 5/2017 | Schonholz | |
| 2017/0232189 A1 | 8/2017 | Qin et al. | |
| 2017/0296714 A1 | 10/2017 | Locke et al. | |
| 2017/0319761 A1 | 11/2017 | Locke et al. | |
| 2017/0326277 A1 | 11/2017 | Huang | |
| 2017/0368239 A1 | 12/2017 | Askem et al. | |
| 2018/0008760 A1 | 1/2018 | Zilbershlag et al. | |
| 2018/0021178 A1 | 1/2018 | Locke et al. | |
| 2018/0028728 A1 | 2/2018 | Aarestad et al. | |
| 2018/0104393 A1 | 4/2018 | Wu et al. | |
| 2018/0200414 A1 | 7/2018 | Askem et al. | |
| 2018/0272052 A1 | 9/2018 | Locke et al. | |
| 2018/0296397 A1 | 10/2018 | Askem et al. | |
| 2018/0318137 A1 | 11/2018 | Donda et al. | |
| 2018/0318165 A1 | 11/2018 | Donda et al. | |
| 2018/0353771 A1 | 12/2018 | Kim et al. | |
| 2019/0021911 A1 | 1/2019 | Askem et al. | |
| 2019/0076298 A1 | 3/2019 | Quintanar et al. | |
| 2019/0091382 A1* | 3/2019 | Middaugh | A61M 1/964 |
| 2019/0125943 A1 | 5/2019 | Askem et al. | |
| 2019/0142644 A1 | 5/2019 | Askem et al. | |
| 2019/0143007 A1 | 5/2019 | Askem et al. | |
| 2019/0159938 A1 | 5/2019 | Askem et al. | |
| 2019/0192350 A1 | 6/2019 | Gowans et al. | |
| 2019/0282737 A1 | 9/2019 | Beadle et al. | |
| 2019/0298895 A1* | 10/2019 | Selby | A61M 1/88 |
| 2020/0022846 A1 | 1/2020 | Beadle et al. | |
| 2021/0001022 A1 | 1/2021 | Lin | |

FOREIGN PATENT DOCUMENTS

| | | | |
|---|---|---|---|
| DE | 19844355 | A1 | 4/2000 |
| EP | 0512543 | A2 | 11/1992 |
| EP | 1411874 | A1 | 4/2004 |
| EP | 1455701 | B1 | 3/2006 |
| EP | 1807032 | A1 | 7/2007 |
| EP | 1476217 | B1 | 3/2008 |
| EP | 1507498 | B1 | 7/2009 |
| EP | 1791579 | B1 | 7/2009 |
| EP | 2109472 | A1 | 10/2009 |
| EP | 1947987 | B1 | 5/2010 |
| EP | 1358456 | B1 | 7/2010 |
| EP | 2214728 | A2 | 8/2010 |
| EP | 2254537 | A2 | 12/2010 |
| EP | 2279016 | A1 | 2/2011 |
| EP | 2340064 | A1 | 7/2011 |
| EP | 2346468 | A2 | 7/2011 |
| EP | 2349155 | A2 | 8/2011 |
| EP | 1814609 | B2 | 9/2011 |
| EP | 2205190 | B1 | 9/2011 |
| EP | 2370116 | A2 | 10/2011 |
| EP | 2531761 | A1 | 12/2012 |
| EP | 2231088 | B1 | 1/2013 |
| EP | 2015655 | B1 | 3/2013 |
| EP | 2285323 | B1 | 3/2013 |
| EP | 2563421 | A1 | 3/2013 |
| EP | 2049055 | B1 | 4/2013 |
| EP | 2340066 | B1 | 4/2013 |
| EP | 2440260 | B1 | 5/2013 |
| EP | 2340062 | B1 | 6/2013 |
| EP | 2603699 | A1 | 6/2013 |
| EP | 1893145 | B1 | 7/2013 |
| EP | 2370142 | B1 | 7/2013 |
| EP | 2279017 | B1 | 8/2013 |
| EP | 2370117 | B1 | 8/2013 |
| EP | 2258443 | B1 | 9/2013 |
| EP | 2659915 | A1 | 11/2013 |
| EP | 1848390 | B1 | 12/2013 |
| EP | 1875081 | B1 | 12/2013 |
| EP | 2271381 | B1 | 12/2013 |
| EP | 2160166 | B1 | 1/2014 |
| EP | 2305325 | B1 | 4/2014 |
| EP | 2323712 | B1 | 4/2014 |
| EP | 2451498 | B1 | 4/2014 |
| EP | 2051675 | B1 | 6/2014 |
| EP | 1485613 | B1 | 7/2014 |
| EP | 1545644 | B1 | 8/2014 |
| EP | 2349154 | B1 | 8/2014 |
| EP | 2146759 | B1 | 9/2014 |
| EP | 2468323 | B1 | 10/2014 |
| EP | 2658493 | B1 | 10/2014 |
| EP | 1850818 | B1 | 12/2014 |
| EP | 2268348 | B1 | 12/2014 |
| EP | 2561128 | B1 | 1/2015 |
| EP | 2683285 | B1 | 2/2015 |
| EP | 2470136 | B1 | 3/2015 |
| EP | 2503974 | B1 | 5/2015 |
| EP | 2249894 | B1 | 8/2015 |
| EP | 2802366 | B1 | 8/2015 |
| EP | 2438302 | B1 | 9/2015 |

(56) References Cited

FOREIGN PATENT DOCUMENTS

| | | |
|---|---|---|
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 2305327 B1 | 10/2016 |
| EP | 2467086 B1 | 10/2016 |
| EP | 2470135 B1 | 10/2016 |
| EP | 2282788 B1 | 12/2016 |
| EP | 2462956 B2 | 3/2017 |
| EP | 3139878 A1 | 3/2017 |
| EP | 1587502 B1 | 5/2017 |
| EP | 1587554 B1 | 5/2017 |
| EP | 2731563 B1 | 5/2017 |
| EP | 2905037 B1 | 5/2017 |
| EP | 2968871 B1 | 7/2017 |
| EP | 2632613 B1 | 8/2017 |
| EP | 2781208 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 2687241 B2 | 11/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 3287113 B1 | 10/2019 |
| EP | 2244756 B1 | 12/2019 |
| EP | 2968702 B1 | 12/2019 |
| EP | 3941402 A1 | 1/2022 |
| FR | 2939320 A1 | 6/2010 |
| GB | 2511523 A | 9/2014 |
| RU | 131622 U1 | 8/2013 |
| WO | WO-2009098696 A2 | 8/2009 |
| WO | WO-2009120951 A2 | 10/2009 |
| WO | WO-2011135285 A1 | 11/2011 |
| WO | WO-2011144888 A1 | 11/2011 |
| WO | WO-2014099709 A1 | 6/2014 |
| WO | WO-2016126560 A1 | 8/2016 |
| WO | WO-2017079174 A1 | 5/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO-2018158250 A1 | 9/2018 |
| WO | WO-2018162613 A1 | 9/2018 |
| WO | WO-2018164803 A1 | 9/2018 |
| WO | WO-2018185138 A1 | 10/2018 |
| WO | WO-2018187394 A1 | 10/2018 |
| WO | WO-2018192978 A1 | 10/2018 |
| WO | WO-2018206420 A1 | 11/2018 |
| WO | WO-2019053101 A1 | 3/2019 |
| WO | WO-2019053106 A1 | 3/2019 |
| WO | WO-2019086341 A1 | 5/2019 |
| WO | WO-2019086475 A1 | 5/2019 |
| WO | WO-2019193141 A1 | 10/2019 |
| WO | WO-2020110626 A1 | 6/2020 |

OTHER PUBLICATIONS

International Preliminary Report on Patentability for Application No. PCT/EP2020/057407, mailed on Sep. 30, 2021, 9 pages.

* cited by examiner

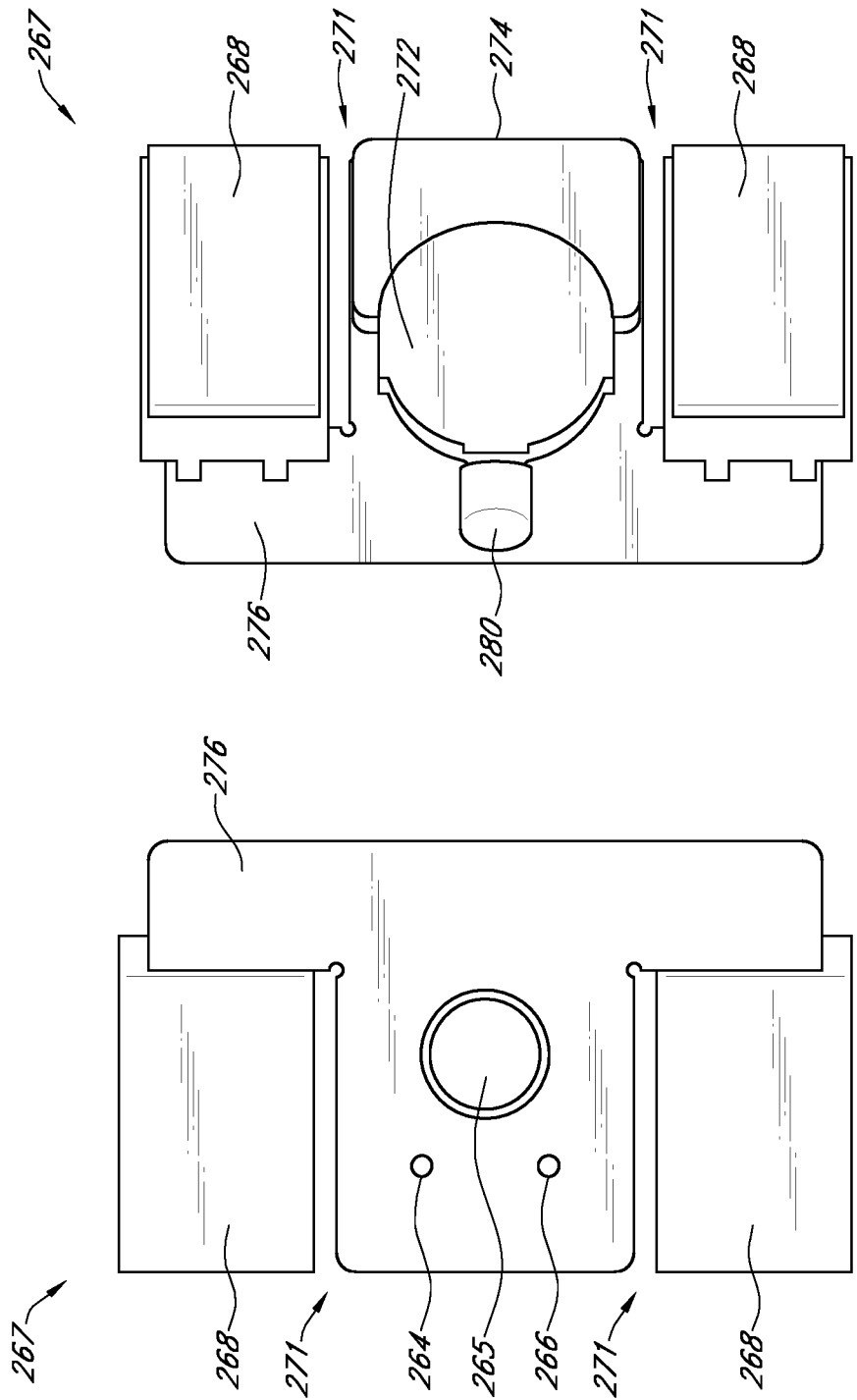

NEGATIVE PRESSURE WOUND TREATMENT APPARATUSES AND METHODS WITH INTEGRATED ELECTRONICS

CROSS-REFERENCE TO RELATED APPLICATIONS

This application is a U.S. national stage application of International Patent Application No. PCT/EP2020/057407, filed Mar. 18, 2020, which claims priority to Great Britain Patent Application No. 1903774.6, filed Mar. 20, 2019 which is hereby incorporated by reference in its entirety and made part of this disclosure.

BACKGROUND

Technical Field

Embodiments described herein relate to apparatuses, systems, and methods the treatment of wounds, for example using dressings in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressings are known for aiding in NPWT systems. These different types of wound dressings include many different types of materials and layers, for example, gauze, pads, foam pads or multi-layer wound dressings. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Prior art dressings for use in negative pressure such as those described above have included a negative pressure source located in a remote location from the wound dressing. Negative pressure sources located remote from the wound dressing have to be held by or attached to the user or other pump support mechanism. Additionally, a tubing or connector is required to connect the remote negative pressure source to the wound dressing. The remote pump and tubing can be cumbersome and difficult to hide in or attach to patient clothing. Depending on the location of the wound dressing, it can be difficult to comfortably and conveniently position the remote pump and tubing. When used, wound exudate may soak into the dressing, and the moisture from the wound has made it difficult to incorporate electronic components into the dressing.

SUMMARY

Embodiments of the present disclosure relate to apparatuses and methods for wound treatment. Some of the wound treatment apparatuses described herein comprise a negative pressure source or a pump system for providing negative pressure to a wound. Wound treatment apparatuses may also comprise wound dressings that may be used in combination with the negative pressure sources and pump assemblies described herein. In some embodiments, a negative pressure source is incorporated into a wound dressing apparatus so that the wound dressing and the negative pressure source are part of an integral or integrated wound dressing structure that applies the wound dressing and the negative pressure source simultaneously to a patient's wound. The negative pressure source and/or electronic components may be positioned between a wound contact layer and a cover layer of the wound dressing. An electronics assembly can be incorporated into a protective enclosure formed at least in part by a film and the film can have apertures of porous material. These and other embodiments as described herein are directed to overcoming particular challenges involved with incorporating a negative pressure source and/or electronic components into a wound dressing.

According to one embodiment, a wound dressing apparatus can comprise a wound contact layer comprising a proximal wound-facing face and a distal face, wherein the proximal wound-facing face is configured to be positioned in contact with a wound, at least one absorbent layer over the wound contact layer, a cover layer configured to cover and form a seal over the wound contact layer and the at least one absorbent layer, an electronics assembly comprising an electronics unit comprising a negative pressure source, and a plate or label, wherein the cover layer comprises at least one opening configured to receive the electronics assembly, a preshaped film, wherein the film is formed to be inserted into the at least one opening, wherein the film comprises an aperture and the at least one absorbent layer is configured to be in fluid communication with the aperture, wherein the electronics assembly is configured to be placed over the film in the at least one opening and the electronics unit is enclosed within the film and the plate or label.

The wound dressing apparatus of the preceding paragraph or in other embodiments can include one or more of the following features. The preshaped film can be thermoformed. The preshaped film can be vacuum formed. The at least one absorbent layer can comprise at least one opening configured to receive the electronics assembly. The apparatus can comprise a porous material in the aperture of the film, wherein the porous material is configured to prevent wound exudate from entering the negative pressure source. The apparatus can comprise a hydrophobic material in the aperture configured to prevent wound exudate from entering the negative pressure source. The aperture can comprise a bacterial filter. The apparatus can comprise a three-dimensional porous material in the aperture, wherein the three-dimensional porous material is configured to receive an inlet of the negative pressure source, wherein the three-dimensional porous material is configured to prevent wound exudate from entering the negative pressure source. The three-dimensional porous material can be sealed to the aperture in the film. The three-dimensional porous material can comprise a port configured to receive the inlet of the negative pressure source in a complementary fit or friction fit engagement. The three-dimensional porous material can circumferentially surround the inlet of the negative pressure source. The three-dimensional porous material can comprise a width, height, and/or length dimension that is greater than the width, height, and/or length of the inlet of the negative pressure source. The three-dimensional porous material can comprise a cuboid or generally cuboid shape. The three-dimensional porous material can comprise a flat negative pressure source-facing surface through which the port extends and one or more beveled edges and/or corners. The wound dressing can further comprise a transmission layer comprising a proximal wound-facing face and a distal face, the transmission layer positioned over the distal face of the wound contact layer. The at least one absorbent layer can comprise a first absorbent layer comprising a proximal wound-facing face and a distal face, the first absorbent layer positioned on the distal face of the transmission layer and a second absorbent comprising a proximal wound-facing face and a distal face, the second absorbent layer positioned on the distal face of the first absorbent layer.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

FIGS. 2A-2B illustrate embodiments of an electronics unit incorporated into a wound dressing;

DETAILED DESCRIPTION

Figure 1A:
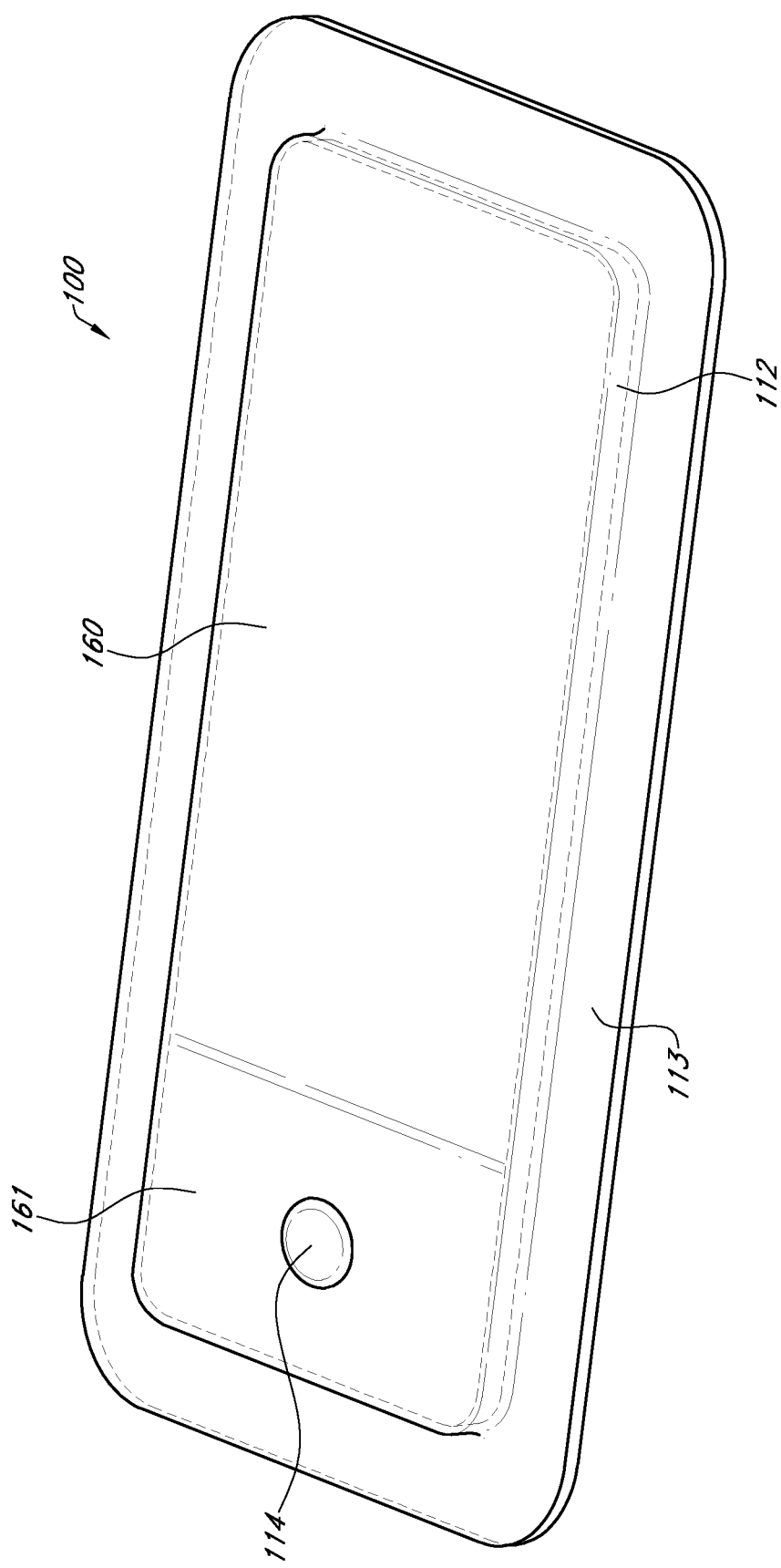
FIGS. 1A-1C illustrates a wound dressing incorporating the source of negative pressure and/or other electronic components within the wound dressing.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressings, wound treatment apparatuses and methods described herein may also be used in combination or in addition to those described in International Application No. PCT/M2013/001469, filed May 22, 2013, titled "APPARATUSES AND METHODS FOR NEGATIVE PRESSURE WOUND THERAPY," published as WO 2013/175306 on Nov. 28, 2013, U.S. patent application Ser. No. 14/418,874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418,908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. Application No. 2015/0182677, published Jul. 2, 2015, titled "WOUND DRESSING AND METHOD OF TREATMENT," the disclosures of which are hereby incorporated by reference in their entireties. Embodiments of the wound dressings, wound treatment apparatuses and methods described herein may also be used in combination or in addition to those described in U.S. patent application Ser. No. 13/092,042, filed Apr. 21, 2011, published as U.S. 2011/0282309, titled "WOUND DRESSING AND METHOD OF USE," and which is hereby incorporated by reference in its entirety, including further details relating to embodiments of wound dressings, the wound dressing components and principles, and the materials used for the wound dressings.

Embodiments of the wound dressings, wound treatment apparatuses and methods described herein relating to wound dressings with electronics incorporated into the dressing may also be used in combination or in addition to those described in PCT Application Number PCT/EP2017/055225, filed Mar. 6, 2017, titled "WOUND TREATMENT APPARATUSES AND METHODS WITH NEGATIVE PRESSURE SOURCE INTEGRATED INTO WOUND DRESSING," and which is hereby incorporated by reference in its entirety, including further details relating to embodiments of wound dressings, the wound dressing components and principles, and the materials used for the wound dressings.

Figure 1B:
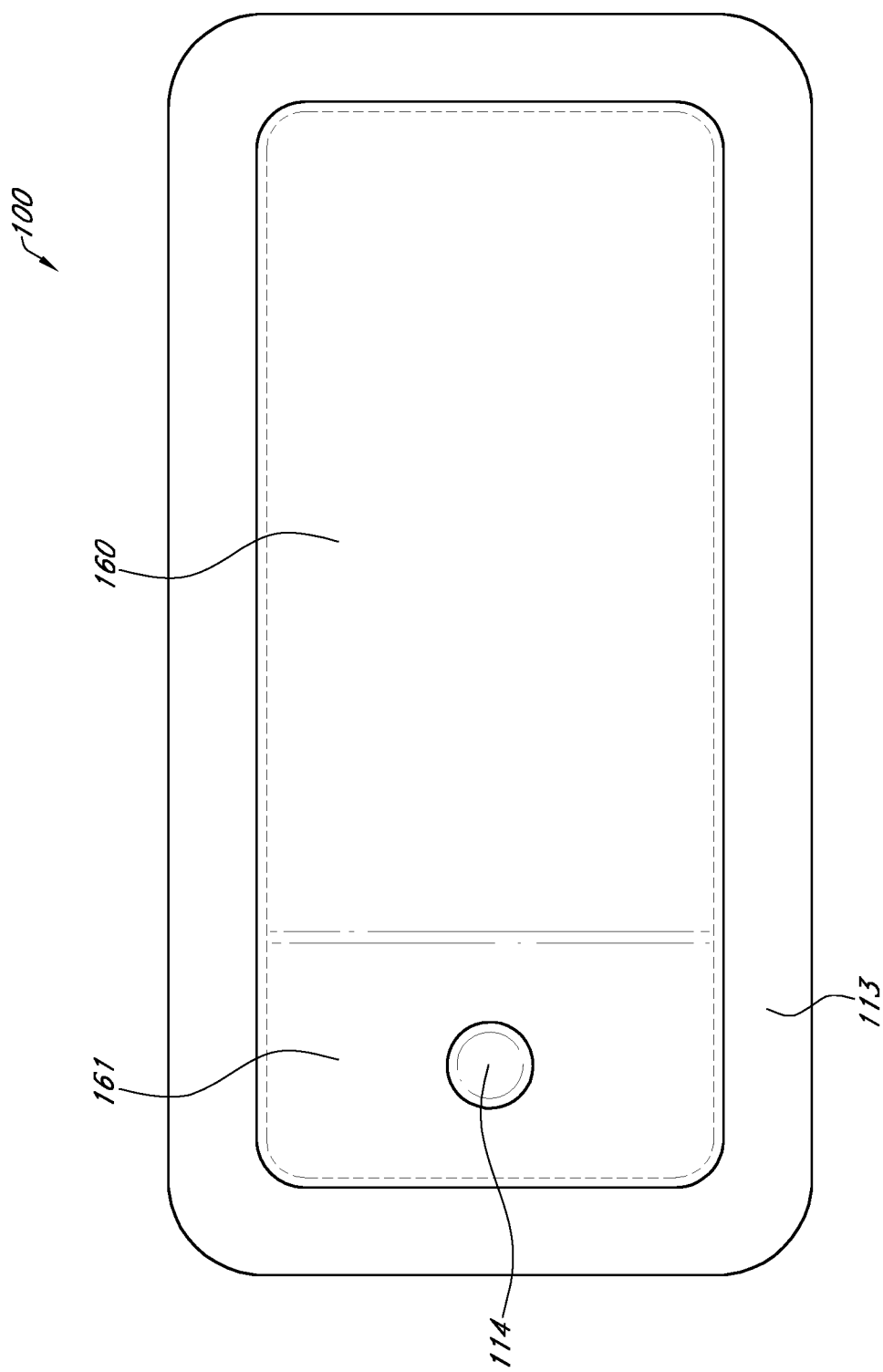
Figure 1C:
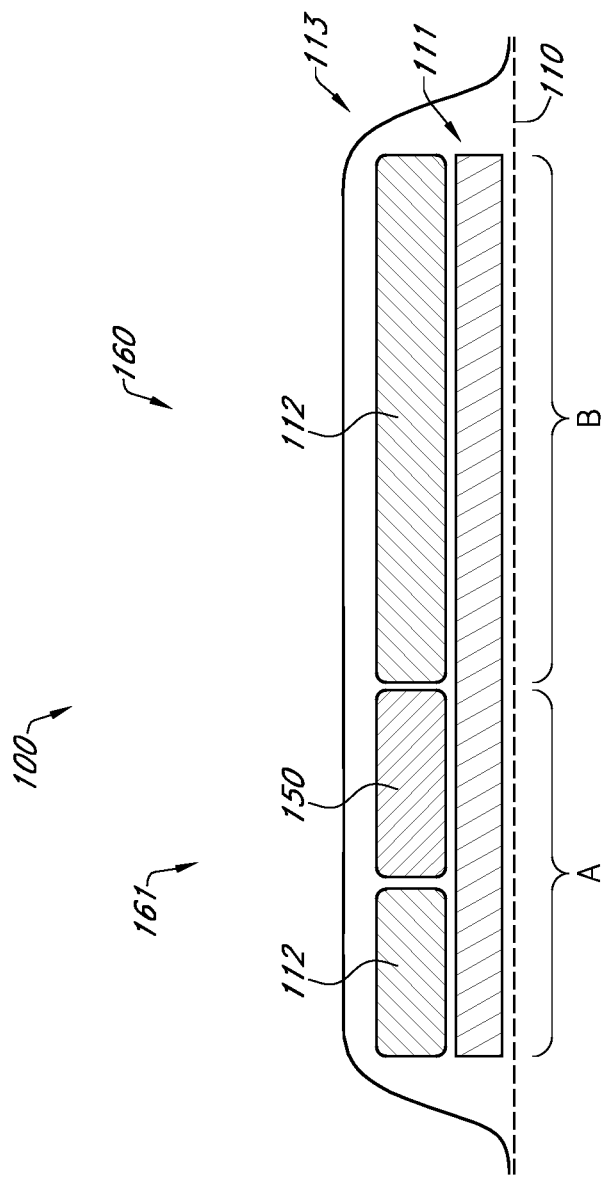

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include various material layers described here and described in further detail in International Application No. PCT/EP2017/055225, filed Mar. 6, 2017, entitled WOUND TREATMENT APPARATUSES AND METHODS WITH NEGATIVE PRESSURE SOURCE INTEGRATED INTO WOUND DRESSING. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. In some embodiments, the dressing can be provided as a single article with all wound dressing elements (including the pump) pre-attached and integrated into a single unit. In some embodiments, a periphery of the wound contact layer can be attached to the periphery of the cover layer enclosing all wound dressing elements as illustrated in FIG. 1A-1C.

In some embodiments, the pump and/or other electronic components can be configured to be positioned adjacent to or next to the absorbent and/or transmission layers so that the pump and/or other electronic components are still part of a single article to be applied to a patient. In some embodiments, the pump and/or other electronics can be positioned away from the wound site. FIGS. 1A-1C illustrates a wound dressing incorporating the source of negative pressure and/or other electronic components within the wound dressing. FIGS. 1A-1C illustrates a wound dressing 100 with the pump and/or other electronics positioned away from the wound site. The wound dressing can include an electronics area 161 and an absorbent area 160. The dressing can comprise a wound contact layer 110 (not shown in FIGS.

1A-1B) and a moisture vapor permeable film or cover layer 113 positioned above the contact layer and other layers of the dressing. The wound dressing layers and components of the electronics area as well as the absorbent area can be covered by one continuous cover layer 113 as shown in FIGS. 1A-1C.

The dressing can comprise a wound contact layer 110, a transmission layer 111, an absorbent layer 112, a moisture vapor permeable film or cover layer 113 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound.

The wound contact layer 110 can be a polyurethane layer or polyethylene layer or other flexible layer which is perforated, for example via a hot pin process, laser ablation process, ultrasound process or in some other way or otherwise made permeable to liquid and gas. The wound contact layer 110 has a lower surface and an upper surface. The perforations preferably comprise through holes in the wound contact layer 110 which enable fluid to flow through the layer 110. The wound contact layer 110 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 110 may help maintain the integrity of the entire dressing 100 while also creating an air tight seal around the absorbent pad in order to maintain negative pressure at the wound.

Some embodiments of the wound contact layer 110 may also act as a carrier for an optional lower and upper adhesive layer (not shown). For example, a lower pressure sensitive adhesive may be provided on the lower surface of the wound dressing 100 whilst an upper pressure sensitive adhesive layer may be provided on the upper surface of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized it may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

The transmission layer assists in distributing negative pressure over the wound site and facilitating transport of wound exudate and fluids into the wound dressing. In some embodiments, the transmission layer can be formed at least partially from a three dimensional (3D) fabric.

In some embodiments, the transmission layer 111 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 112 helps lock the liquid away or itself wicks the liquid onwards towards the cover layer 113 where it can be transpired.

Preferably, to improve the liquid flow across the transmission layer 111 (that is to say perpendicular to the channel region formed between the top and bottom spacer layers), the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Further, an absorbent layer (such as layer 112) for absorbing and retaining exudate aspirated from the wound can be utilized. In some embodiments, a superabsorbent material can be used in the absorbent layer 112. In some embodiments, the absorbent includes a shaped form of a superabsorber layer.

A layer 112 of absorbent material is provided above the transmission layer 111. The absorbent material, which comprise a foam or non-woven natural or synthetic material, and which may optionally comprise a super-absorbent material, forms a reservoir for fluid, particularly liquid, removed from the wound site. In some embodiments, the layer 111 may also aid in drawing fluids towards the cover layer 113.

The material of the absorbent layer 112 may also prevent liquid collected in the wound dressing from flowing freely within the dressing, and preferably acts so as to contain any liquid collected within the dressing. The absorbent layer 112 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 112 may typically be manufactured from ALLEVYN™ foam, Freudenberg 114-224-4 or Chem-Posite™ 11C-450. In some embodiments, the absorbent layer 112 may comprise a composite comprising superabsorbent powder, fibrous material such as cellulose, and bonding fibers. In a preferred embodiment, the composite is an airlaid, thermally-bonded composite.

In some embodiments, the absorbent layer 112 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

The wound dressing layers of the electronics area and the absorbent layer can be covered by one continuous cover layer or backing layer 113. As used herein, the terms cover layer and/or backing layer can be used interchangeably to refer to the layer of material in the dressing configured to cover the underlying dressing layers and seal to the wound contact layer and/or the skin surrounding the wound. In some embodiments, the cover layer can include a moisture vapor permeable material that prevents liquid exudate removed from the wound and other liquids from passing through, while allowing gases through.

The cover layer 113 is preferably gas impermeable, but moisture vapor permeable, and can extend across the width of the wound dressing 100. The cover layer 113, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer 113 and a wound site where a negative pressure can be established. The cover layer 113 is preferably sealed to the wound contact layer 110 in a border region around the circumference of the dressing, ensuring that no air is drawn in through the border area, for example via adhesive or welding techniques. The cover layer 113 protects the wound from external bacterial contamination (bacterial barrier) and allows liquid from wound exudates to be transferred through the layer and evaporated from the film outer surface. The cover layer 113 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the cover layer increases when the cover layer becomes wet. The moisture vapor permeability of the wet cover layer may be up to about ten times more than the moisture vapor permeability of the dry cover layer.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 114 as shown in FIGS. 1A-1B. The button or switch 114 can be used for operating the pump (e.g., turning the pump on/off).

The absorbent area 160 can include an absorbent material 112 and can be positioned over the wound site. The electronics area 161 can be positioned away from the wound site, such as by being located off to the side from the absorbent area 160. The electronics area 161 can be positioned adjacent to and in fluid communication with the absorbent area 160 as shown in FIGS. 1A-1C. In some embodiments, each of the electronics area 161 and absorbent area 160 may be rectangular in shape and positioned adjacent to one another. In FIG. 1C, the electronics area 161 is noted as area "A" and the absorbent area 160 is noted as area "B". In some embodiments, as illustrated in FIG. 1C, electronic components 150 can be positioned within a recess or cut out of the absorbent material 112 but off to the side of the absorbent area. As shown in the cross sectional view of the wound dressing layers in FIG. 1C, the absorbent material 112 can be positioned on both sides of the electronic components 150.

In some embodiments, additional layers of dressing material can be included in the electronics area 161, the absorbent area 160, or both areas. In some embodiments, the dressing can comprise one or more transmission or spacer layers and/or one or more absorbent layer positioned above the wound contact layer 110 and below the cover layer 113 of the dressing.

In some embodiments, the electronics area 161 of the dressing can comprise electronic components 150. In some embodiments, the electronics area 161 of the dressing can comprise one or more layers of transmission or spacer material and/or absorbent material and electronic components 150 can be embedded within the one or more layers of transmission or spacer material and/or absorbent material. The layers of transmission or absorbent material can have recesses or cut outs to embed the electronic components 150 within whilst providing structure to prevent collapse. The electronic components 150 can include a pump, power source, controller, and/or an electronics package.

A pump exhaust can be provided to exhaust air from the pump to the outside of the dressing. The pump exhaust can be in communication with the electronics area 161 and the outside of the dressing.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

FIG. 1A-1C illustrates a wound dressing apparatus incorporating the pump and/or other electronic components within the wound dressing and offset from the absorbent layer. In some embodiments, as shown in FIG. 1C, the absorbent area 160 comprises a transmission layer 111 positioned above the wound contact layer 110. An absorbent layer 112 can be provided above the transmission layer 111. In some embodiments, the electronics area 161 can include an electronics unit (shown in FIGS. 2A-2B). In some embodiments, the electronics unit is provided directly over the wound contact layer. In other embodiments, the electronics unit can be placed above a layer of wicking material, absorbent material, or transmission material that sits above the wound contact layer 110 of the dressing. For example, as shown in FIG. 1C, the electronics unit 150 may be positioned over the transmission layer 111. In some embodiments, the transmission layer 111 can be a single layer of material extending below the electronics unit 150 and the absorbent material 112. Thus, in some embodiments, the transmission layer 111 extends continuously through the absorbent area 160 and the electronics area 161. In alternative embodiments, the transmission layer below the electronics unit can be a different transmission layer than the transmission layer below the absorbent material 112. The transmission layer 111, absorbent material 112, and electronics unit 150 can be covered with a cover layer 113 that seals to a perimeter of the wound contact layer 110 as shown in FIGS. 1A-1C.

The electronics area 161 can include an electronics unit 150 positioned below the cover layer 113 of the dressing. In some embodiments, the electronics unit can be surrounded by a material to enclose or encapsulate a negative pressure source and electronics components by surrounding the electronics. In some embodiments, this material can be a casing. In some embodiments, the electronics unit can be encapsulated or surrounded by a protective coating, for example, a hydrophobic coating as described herein. The electronics unit can be in contact with the dressing layers in the absorbent area 160 and covered by the cover layer 113. As used herein, the electronics unit includes a lower or wound facing surface that is closest to the wound and an opposite, upper surface, furthest from the wound when the wound dressing is placed over a wound.

FIG. 1C illustrates an embodiment of a wound dressing incorporating an electronics unit 150 within the dressing. In some embodiments, the electronics sub assembly or electronics unit 150 can be embedded in an aperture or hole in an absorbent layer 112 towards one end of the dressing, as depicted in FIG. 1C.

In some embodiments, the absorbent components and electronics components can be overlapping but offset. For example, a portion of the electronics area can overlap the absorbent area, for example overlapping the superabsorber layer, but the electronics area is not completely over the absorbent area. Therefore, a portion of the electronics area can be offset from the absorbent area. The dressing layer and electronic components can be enclosed in a wound contact layer 110 positioned below the lower most layer and a cover layer 113 positioned above the absorbent layer 112 and electronics 150. The wound contact layer 110 and cover layer 113 can be sealed at a perimeter enclosing the dressing components. In some embodiments, the cover layer can be in direct physical contact with the absorbent material, and/or the electronics unit. In some embodiments, the cover layer can be sealed to a portion of the electronics unit and/or casing, for example, in areas where holes or apertures are used to accommodate the electronic components (e.g. a switch and/or exhaust).

FIGS. 2A-2B illustrate embodiments of an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more batteries 268. The electronics unit 267 can include a flexible circuit board 276 configured to be in electrical communication with the pump 272 and/or batteries 268.

As illustrated in FIG. 2A, the electronics unit 267 can include single button or switch 265 on the upper surface of the unit. The single button or switch 265 can be used as an on/off button or switch to stop and start operation of the pump and/or electronic components. The switch 265 can be a dome type switch configured to sit on the top of the pump. Because the switch is situated within the dressing the cover layer can be easily sealed around or over the switch. In some embodiments, the cover layer can have an opening or hole positioned above the switch. The cover layer can be sealed to the outer perimeter of the switch 265 to maintain negative pressure under the wound cover. The switch can be placed on any surface of the electronics unit and can be in electrical connection with the pump.

Figure 3A:
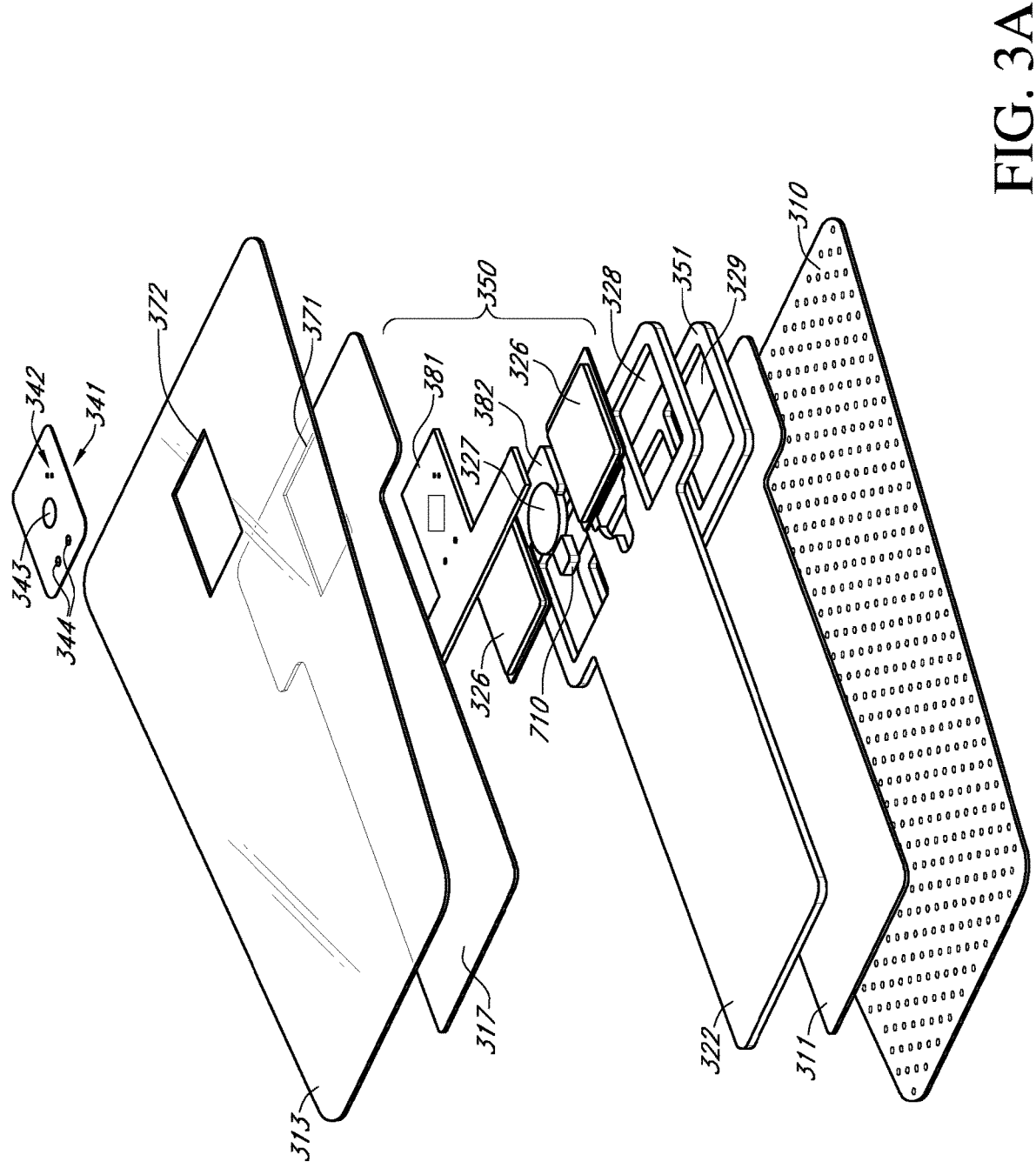
FIG. 3A illustrates an embodiment of wound dressing layers incorporating the electronic components within the wound dressing.

The electronics unit 267 can also include one or more vents or exhausts aperture 264 on the flexible circuit board for expelling the air exhausted from the pump. As shown in FIG. 2B, a pump outlet exhaust mechanism 274 can be attached to the outlet of the pump 272. The vent or exhaust aperture 264 can be in fluid communication with a pump exhaust mechanism 274 positioned at the outlet of the pump and extending to the lower surface of the flexible circuit board. In some embodiments, an exhaust vent 264 on the flexible circuit board can provide communication with the top surface of the dressing and allow the pump exhaust to be vented from the electronics unit. In some embodiments, the exhaust mechanism 274 can be attached to the outlet end of the pump and can extend out from the pump at a 90-degree angle from the pump orientation to communicate with the bottom surface of the flexible circuit board. In some embodiments, the exhaust mechanism 274 can include an antibacterial membrane and/or a non-return valve. In some embodiments, the exhaust vent 264 can include an antibacterial membrane and/or a non-return valve. The exhausted air from the pump can pass through the pump outlet and exhaust mechanism 274. In some embodiments, the cover layer 113 can include apertures or holes positioned above the exhaust vent 264 and/or membrane. The cover layer 113 can be sealed to the outer perimeter of the exhaust 264 to maintain negative pressure under the wound cover 113. In some embodiments, the exhausted air can be exhausted through the gas permeable material or moisture vapor permeable material of the cover layer. In some embodiments, the cover layer does not need to contain apertures or holes over the exhaust and the exhausted air is expelled through the cover layer. In some embodiments, the pump outlet mechanism 274 can be a custom part formed to fit around the pump as shown in FIG. 2B. The electronic unit 267 can include a pump inlet protection mechanism 280 positioned on the portion of the electronic unit closest to the absorbent area (as shown in FIG. 3A with the pump inlet protection mechanism 710) and aligned with the inlet of the pump. The pump inlet protection mechanism 280 is positioned between the pump inlet and the absorbent area or absorbent layer of the dressing. The pump inlet protection mechanism 280 can be formed of a hydrophobic material to prevent fluid from entering the pump 272.

In some embodiments, the upper surface of the electronics unit can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (e.g. dressing leak, saturation level of the dressing, and/or low battery).

FIG. 2A-2B illustrates an embodiment of an electronics unit 267. The electronics unit 267 can include a pump 272 and one or more batteries 268 or other power source to power the pump 272 and other electronics. The pump can operate at about 27 volts or about 30 volts. The two batteries can allow for a more efficient voltage increase (6 volts to 30 volts) than would be possible with a single battery.

The batteries 268 can be in electrical communication with a flexible circuit board 276. In some embodiments, one or more battery connections are connected to a surface of the flexible circuit board 276. In some embodiments, the flexible circuit board can have other electronics incorporated within. For example, the flexible circuit board may have various sensors including, but not limited to, one or more pressure sensors, temperature sensors, optic sensors and/or cameras, and/or saturation indicators.

In such embodiments, the components of the electronics unit 267 may include a protective coating to protect the electronics from the fluid within the dressing. The coating can provide a means of fluid separation between the electronics unit 267 and the absorbent materials of the dressing. The coating can be a hydrophobic coating including, but not limited to, a silicone coating or polyurethane coating. In some embodiments, the electronics unit 267 can be encapsulated in a protective housing or enclosure as described in more detail herein. The pump inlet component or pump inlet protection mechanism can be used to protect the pump from fluid on the inlet and the pump outlet mechanism can include a non-return valve that protects fluid from entering the outlet as described in more detail with reference to PCT International Application No. PCT/EP2017/055225, filed Mar. 6, 2017, titled WOUND TREATMENT APPARATUSES AND METHODS WITH NEGATIVE PRESSURE SOURCE INTEGRATED INTO WOUND DRESSING and PCT International Application No. PCT/EP2017/059883, filed Apr. 26, 2017, titled WOUND DRESSINGS AND METHODS OF USE WITH INTEGRATED NEGATIVE PRESSURE SOURCE HAVING A FLUID INGRESS INHIBITION COMPONENT, which are hereby incorporated by reference in their entireties. The pump inlet component or pump inlet protection mechanism can be a component that inhibits fluid ingress. The pump inlet component or pump inlet protection mechanism can allow gas (e.g., air) but inhibit liquid (e.g., wound exudate) from passing through. The pump inlet component or pump inlet protection mechanism can be a porous structure that provides a plurality of flow paths between an interior of the wound dressing and the pump. The plurality of flow paths can inhibit occlusion (e.g., from wound exudate) of the pump. In some embodiments, the component can be made of or coated with a hydrophobic material that repels wound exudate, thereby inhibiting the ingress of fluid into the component and ultimately the pump.

The electronics unit 267 includes one or more slits, grooves or recesses 271 in the unit between the pump and the two batteries. The slits, grooves or recesses 271 can allow for the electronics unit 267 to be flexible and conform to the shape of the wound. The unit 267 can have two parallel slits, grooves or recesses 271 forming three segments of the electronics unit 267. The slits, grooves or recesses 271 of the unit 267 create hinge points or gaps that allows for flexibility of the electronics unit at that hinge point. The pump exhaust vent 264, switch 265, and indicator 266 are shown on the top surface of the electronics unit 267. As illustrated, one embodiment of the electronics unit 267 has two hinge points to separate the unit into three regions or panels, for example one to contain one battery, one to contain the pump, and one to contain another battery. In some embodiments, the slits, grooves or recesses may extend parallel with a longitudinal axis of the dressing that extends along the length of the dressing through the electronics area of the dressing through the absorbent area of the dressing.

FIG. 3A illustrates an embodiment of wound dressing layers incorporating the electronic components within the wound dressing. FIG. 3A illustrates a wound dressing with a wound contact layer 310 configured to contact the wound. The wound contact layer 310 can be a similar material and have a similar function as the wound contact layer described with reference to FIGS. 1A-1C. A transmission layer or spacer layer 311 is provided over the wound contact layer. The transmission layer or spacer layer 311 can be a similar material and have a similar function as the transmission layer or spacer layer described with reference to FIGS. 1A-1C. The transmission layer 311 can assist in transmitting and distributing negative pressure over the wound site.

A first layer of apertured absorbent material 351 can be provided over the transmission layer 311. The first apertured absorbent layer 351 can include one or more apertures 329. In some embodiments, the apertures 329 can be sized and shaped to fit the electronics unit 350 therein. The first apertured absorbent layer 351 can be sized and shaped to the size of the electronics area and does not extend into the absorbent area. In some embodiments, the apertures 329 can be shaped and sized to fit the individual components of the electronics unit 350.

A second apertured absorbent layer 322 can be provided over the first absorbent layer 351. In some embodiments, the second absorbent layer 322 includes one or more apertures 328. The second absorbent layer 322 can be sized and shaped to the size of the electronics area and the absorbent area. In some embodiments, the apertures 328 can be shaped and sized to fit the individual components of the electronics unit 350. The first and second absorbent layers 351 and 322 can be a similar material and have a similar function as the absorbent layer described with reference to FIGS. 1A-1C.

An electronics unit 350 can be positioned in the apertures 328 and 329 of the first and second absorbent material 351 and 322. The electronics unit 350 can be similar to the electronics unit described with reference to FIGS. 2A-2B. The electronics unit 350 can include a pump 327, power source 326, and a printed circuit board 381. In some embodiments, the pump 327 can include a pump inlet mechanism 710 and an outlet mechanism 382. In some embodiments, the printed circuit board 381 can include electronics including but not limited to a switch, sensors, and LEDs as described herein. In some embodiments, the circuit board 381 can include one or more hole to be positioned over one or more exhaust vents (not shown) in the outlet mechanism 382 as described in more detail herein.

An overlay layer 317 can be provided over the electronics components 350 and absorbent layer 322. In some embodiments, the overlay layer 317 can be one or more layers of absorbent and/or transmission material as described herein. In some embodiments, the overlay layer 317 can comprise a conformable material overlaying and overbordering the perimeter of the lower layers of transmission and absorbent materials. In some embodiments, the overlay layer 317 can soften the edges of the wound dressing layers by decreasing the profile around the edges of the dressing layers. The overlay layer 317 can protect the cover layer from being punctured by the lower layers when the cover layer is sealed over the dressing layers below. The overlay layer 317 can include an aperture 371 to allow access to at least a portion of the electronics unit 350 positioned below.

A cover layer or backing layer 313 can be positioned over the overlay layer 317. The cover layer or backing layer 313 can be a similar material and have a similar function as the cover layer or backing layer described with reference to FIGS. 1A-1C. In some embodiments, when the overlay layer 317 is not used, the cover layer or backing layer 313 can be provided above absorbent layers 322, and/or electronic components 350. The cover layer 313 can form a seal to the wound contact layer 310 at a perimeter region enclosing the overlay layer 317, absorbent layers 322 and 351, electronic components 350, and the transmission layer 311. In some embodiments, the cover layer 313 can be a flexible sheet of material that forms and molds around the dressing components when they are applied to the wound. In other embodiments, the cover layer 313 can be a material that is preformed or premolded to fit around the dressing components as shown in FIG. 3A. As used herein, the terms cover layer and backing layer can be used interchangeably to refer to the layer of material in the dressing configured to cover the layers of the wound dressing.

In some embodiments, the cover layer or backing layer 313 can include an aperture 372. The aperture 372 can be positioned over at least a portion of the aperture 371 in the overlay layer 317 to allow access to at least a portion of the electronics unit 350 positioned below. In some embodiments, the apertures 371 and 372 can allow access to the switch and/or venting holes of the pump exhaust.

A label 341 can be provided over the apertures 371 and 372 and positioned over the exposed portion of the electronic components 350. The label can include the vent holes 342, indicator portions 344, and/or switch cover 343. The indicator portions 344 can include holes or transparent regions 344 for positioning over the one or more indicators or LEDs on the printed circuit board 381 below the label 341. The holes or transparent regions 344 can allow for the indicators or LEDs to be visible through the label 341. In some embodiments, the switch cover 343 can include a dome shaped cover positioned over the switch on the printed circuit board 381. In some embodiments, the label 341 can include embossed features for the switch cover 343. In some embodiments, the embossed features of the switch cover 343 can prevent accidental activation or deactivation of the device. In some embodiments, the switch or switch cover 343 can include a tab on the switch to prevent accidental activation or deactivation. The vent holes 342 of the label can allow exhaust from the pump outlet mechanism to pass through the label and exit the wound dressing to be exhausted to the atmosphere.

In some embodiments, the label can be positioned on top of the cover layer or backing layer 313. The label can seal to the cover layer to form a seal over the wound. In other embodiments, the label 341 can be positioned above the overlay layer 371 and below the cover layer or backing layer 313. In such embodiments, the cover layer 313 can have one or more apertures over one or more components of the label 341. For example, the cover layer 313 can have apertures over the vent holes 342, indicator portions 344, and/or switch cover 343.

Figure 3B:
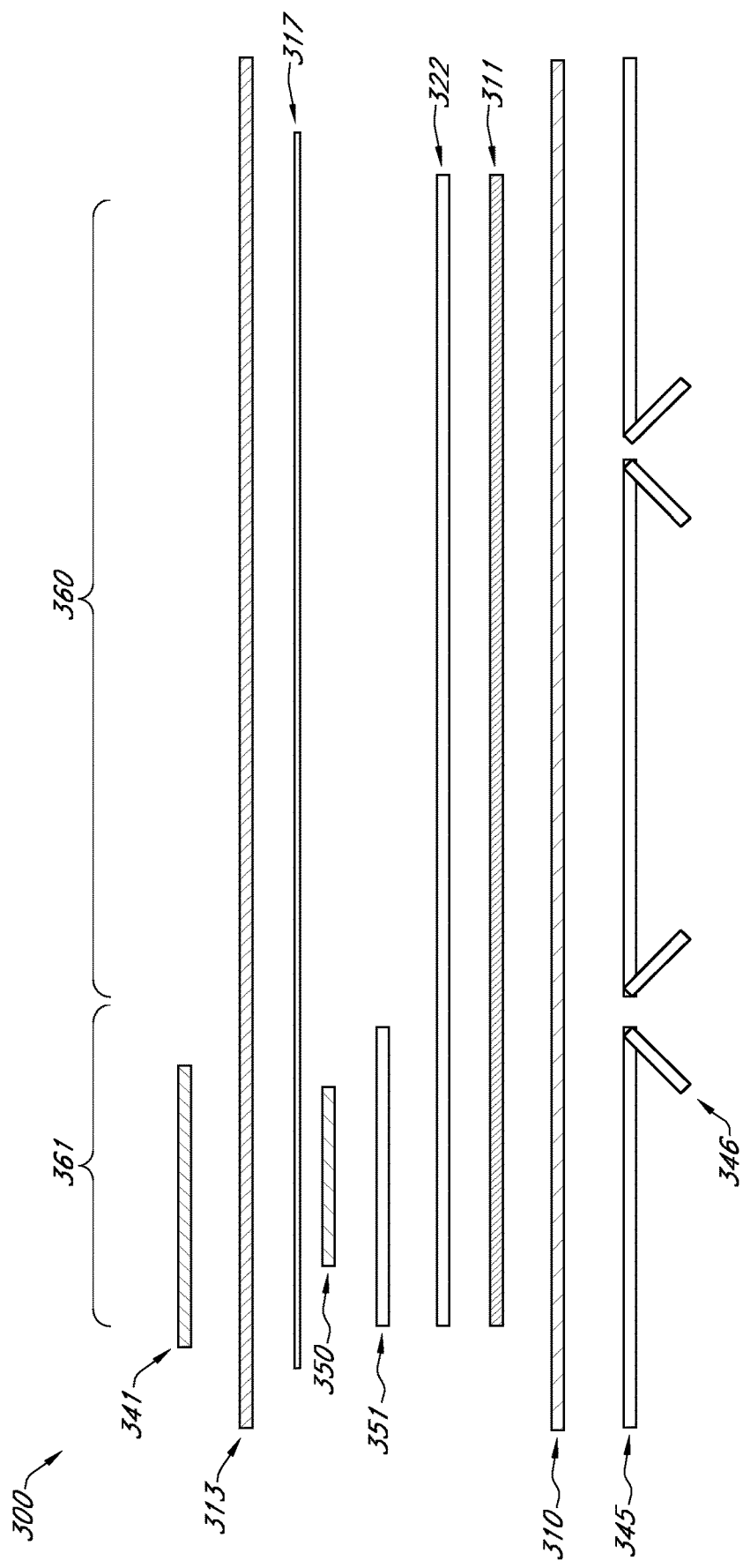
FIG. 3B illustrates a cross sectional layout of the material layers of the wound dressing incorporating an electronics assembly within the dressing.

FIG. 3B illustrates a cross sectional layout of the material layers of the wound dressing incorporating an electronics assembly within the dressing. The dressing 300 included multiple material layers and an electronics assembly 350. The wound dressing 300 can include an electronics area 361 including the electronics and an absorbent area or dressing area 360 that is intended to be applied to the wound as described with reference to FIGS. 1A-1C.

As described herein, the one or more material layers can extend into both the electronics area 361 and the dressing area 360. The dressing 300 can include a wound contact layer 310, transmission layer 311, absorbent layers 322 and 351, an overlay layer 317, and a cover or backing layer 313 as illustrated in FIG. 3B. The absorbent layers 322 and 351 can include recesses or cutouts to receive the components of the electronics assembly 350 as described herein. In some embodiments, as illustrated in FIG. 3B the small apertured absorbent layer 351 can be positioned on top of the large apertured absorbent layer 322. In other embodiments, as illustrated in FIG. 3A the small apertured absorbent layer 351 can be positioned on below of the large apertured absorbent layer 322.

In some embodiments, the overlay layer 317 and/or the cover layer 313 can include a cut out or aperture positioned over the switch and/or indicators of the electronics assembly 350. A label or covering 341 can be positioned over at least a portion of the electronics assembly 350 and any cutouts in the overlay layer 317 and/or the cover layer 313. The label or covering 341 can be similar to the label or covering 341 as described previously with reference to FIG. 3A.

Before use, the dressing can include a delivery layer 345 adhered to the bottom surface of the wound contact layer. The delivery layer 345 can cover adhesive or apertures on the bottom surface of the wound contact layer 310. In some embodiments, the delivery layer 345 can provided support for the dressing and can assist in sterile and appropriate placement of the dressing over the wound and skin of the patient. The delivery layer 345 can include handles 346 that can be used by the user to separate the delivery layer 345 from the wound contact layer 310 before applying the dressing 300 to a wound and skin of a patient.

Figure 3C:
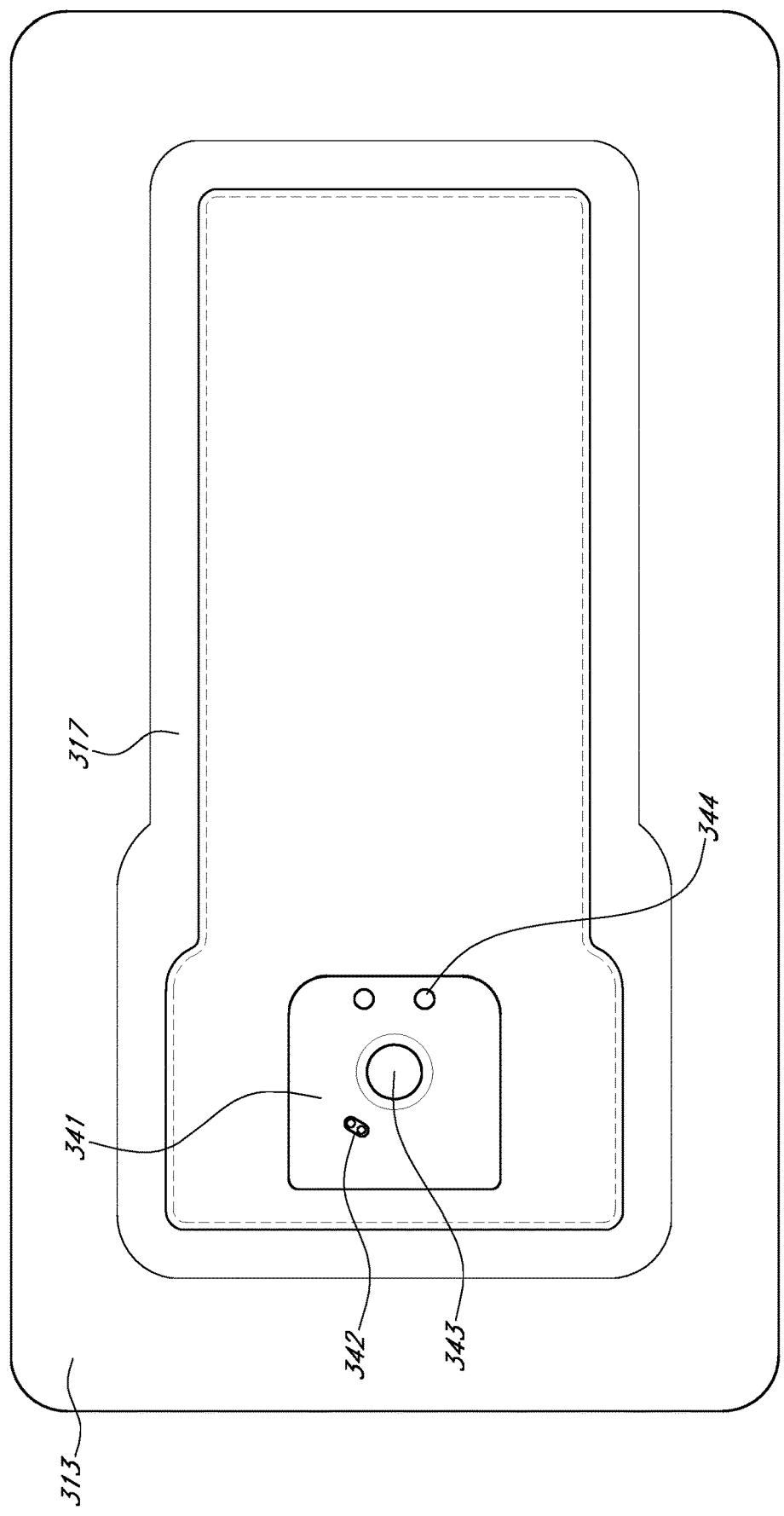
FIG. 3C illustrates a top view of an embodiment of the wound dressing incorporating an electronic assembly within the dressing.

FIG. 3C illustrates a top view of an embodiment of the wound dressing incorporating an electronic assembly within the dressing.

FIG. 3C shows a cover layer 313 and electronics covering 341 covering the overlay layer 317 and underlying dressing and electronics components. The cover layer 313 can seal to the wound contact layer 310 at a perimeter region of the wound contact layer 310. In some embodiments, the label or electronics covering 341 can be positioned over the cover layer 313. In other embodiments, the cover layer 313 can seal over the electronics covering 341. In some embodiments, the cover layer 313 can include one or more holes in the cover layer 313 positioned over the switch and/or pump outlet vent(s). In some embodiments, the cover layer 313 can include a single hole that is positioned over the switch cover 343, visual indicators 344, and/or pump outlet vent(s) 342 in the covering or label 341 as shown in FIG. 3C. In some embodiments, the label can include embossed features for the switch cover 343. In some embodiments, the embossed features of the switch cover 343 can prevent accidental activation or deactivation of the device. In some embodiments, the switch or switch cover 343 can include a tab on the switch to prevent accidental activation or deactivation.

The visual indicators 344 can provide an indication of operation of the negative pressure source and/or an indication of the level of negative pressure that is applied to the wound. In some embodiments, the visual indicators can include one or more light sources or LEDs. In some embodiments, the visual indicator light sources an illuminate to indicate a condition or change of condition. In some embodiments, the light source can illuminate in a particular sequence and/or color that indicates a condition. For example, in some embodiments, the light source can flash to notify the user that the device is operating properly. In some embodiments, the light source can automatically flash periodically and/or the light source can be activated by the switch or other button to light up and indicate a condition.

In some embodiments, the switch can be pressed and/or held down to power the dressing and electronics on and off. In some embodiments, once the switch is activated and the pump and associated colored LED, for example, green colored LED, can be used to confirm the dressing and integrated negative pressure source are operational. In some embodiments, during operation of the pump and dressing, the pump and dressing can enter the fault state indicated by a colored LED, for example, orange colored LED.

Electronic Assembly

The wound dressing described herein can utilize the embedded electronic assembly to generate negative pressure under the dressing. However, it can be important to protect the assembly from wound exudate or other bodily fluids that would corrode the electronics. It can also be important to protect the patient from the electric and electronic components. The electronics assembly can incorporate a pump that pull air from the dressing and exhaust to the environment in order to produce the required negative pressure differential. Therefore, it can be difficult to protect the electronics assembly and allow fluid communication between the electronic assembly and the dressing and environment surrounding the dressing. For example, complete encapsulation or potting of the assembly could prevent the movement of air from the dressing and atmosphere to the pump. In some embodiments, described previously herein, the electronic components of the electronics assembly can be protected from the environment by partial encapsulation, potting, and/or a conformable coating. In some embodiments, potting of electronic components can include a process of filling a complete electronic assembly with a solid or gelatinous compound for resistance to shock and vibration, exclusion of moisture, and/or exclusion of corrosive agents.

Figure 4A:
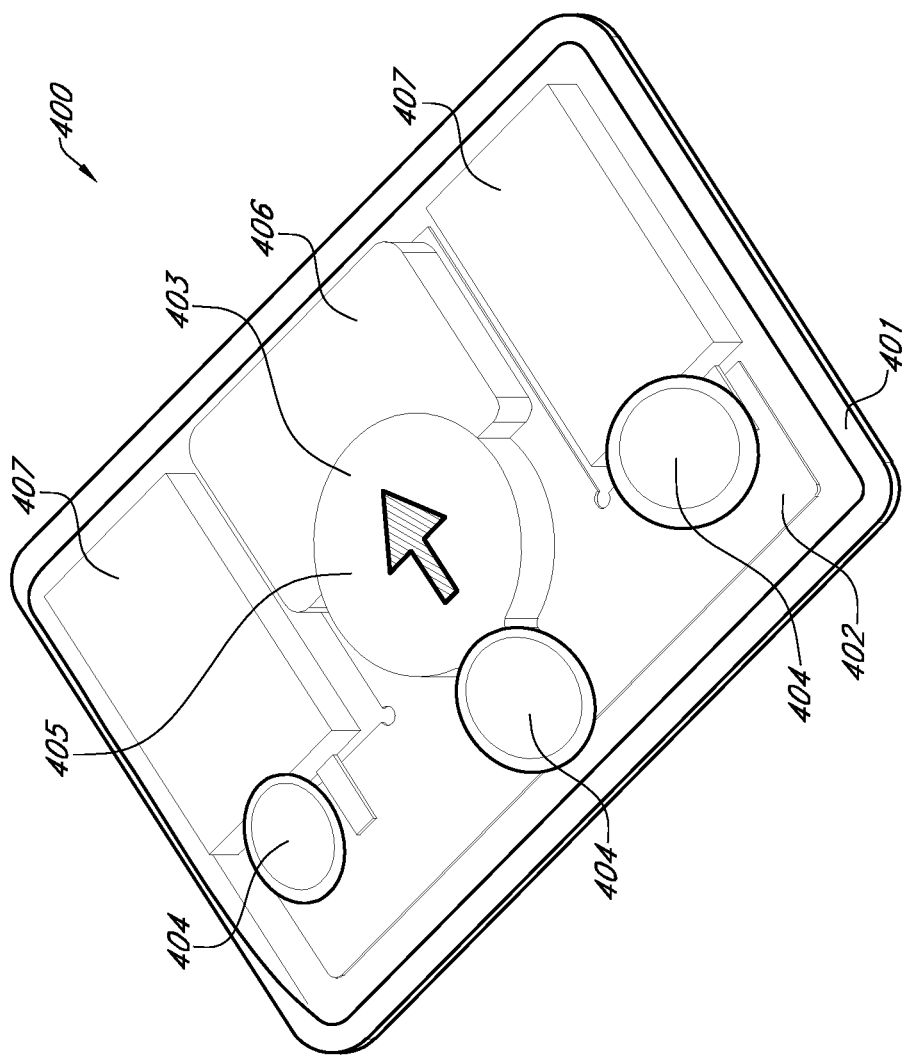
FIGS. 4A and 4B illustrate an embodiment of a housing of the electronics assembly enclosing the electronics unit within.
Figure 4B:
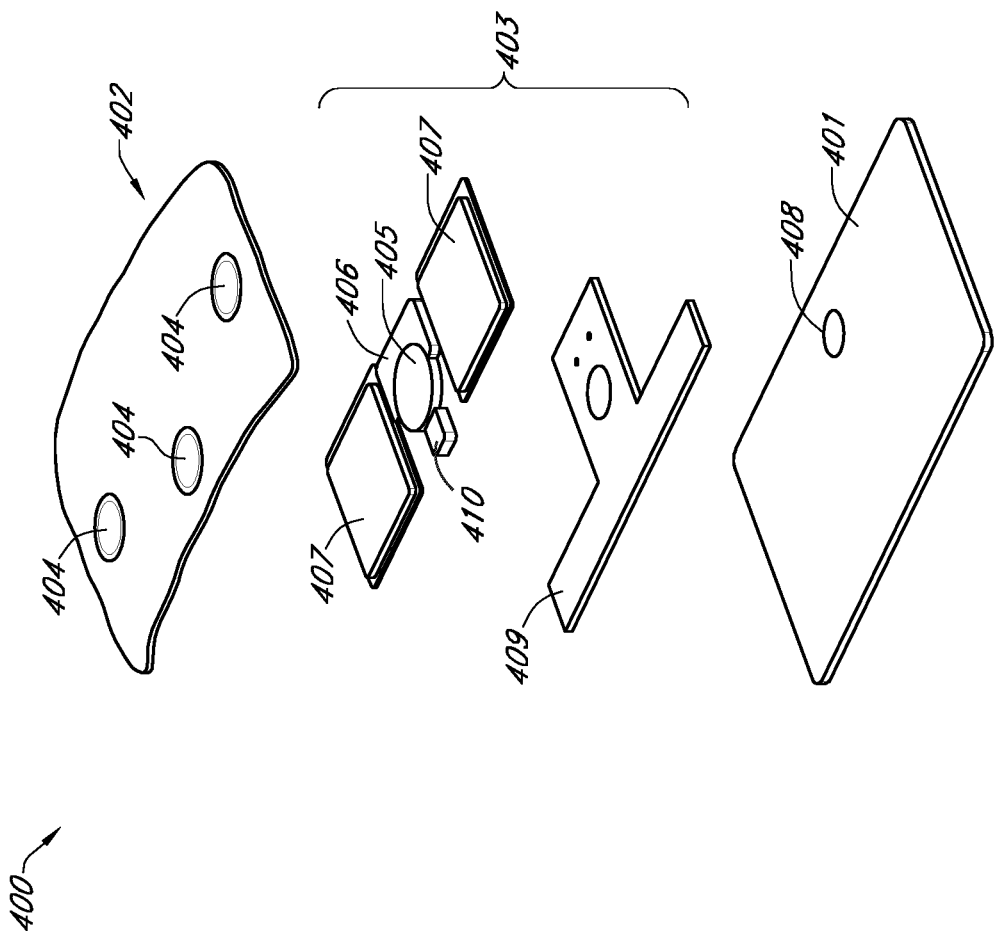

An electronics assembly can be used that includes an electronics unit positioned within an enclosure or housing, as illustrated in FIG. 4A, to be incorporated into a wound dressing. The electronics unit enclosed in the housing can be similar to the electronics unit described with reference to FIGS. 2A-2B but the electronics unit can be positioned within an enclosure or housing. The housing with the electronics unit enclosed within can be placed in the dressing. FIGS. 4A-4B illustrates an embodiment of an electronics assembly 400 enclosing an electronics unit 403 within a housing.

As illustrated in FIGS. 4A and 4B, the housing of the electronics assembly 400 can include a plate 401 and flexible film 402 enclosing the electronics unit 403 within. The electronics unit 403 can include a pump 405, inlet protection mechanism 410 (shown in FIG. 4B), pump exhaust mechanism 406, power source 407, and flexible circuit board 409. In some embodiments, the electronics unit 403 and pump 405 can be used without the inlet protection mechanism 410. The flexible film 402 can be attached to the plate 401 by welding (heat welding) or adhesive bonding to form a fluid tight seal and enclosure around the electronic components. In some embodiments, the flexible film 402 can be attached to the plate at a perimeter of the plate by heat welding, adhesive bonding, ultrasonic welding, RF welding, or any other attachment or bonding technique.

The flexible film 402 can be a flexible plastic polymeric film. In some embodiments, the flexible film 402 can be formed from any material flexible polymeric film or any flexible material that confirms around the electronics. The flexible film can maintain conformability and flexibility while protecting and insulating the components within. In some embodiments, the flexible film 402 can be formed from a flexible or stretchable material, such as one or more of polyurethane, thermoplastic polyurethane (TPU), silicone, polycarbonate, polyethylene, methylated polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. In some embodiments, the flexible film 402 can be formed from polyurethane.

The plate 401 can be a plastic polymer plate. In some embodiments, the plate can be a flexible material to allow conformability to movement or flexing of the dressing when it is applied to a wound. In some embodiments, the plate can be integrated with the components of the label described with reference to FIGS. 3A-3C. In other embodiments, the label can be a separate component attached to the top surface of the plate 401.

The flexible film 402 and plate 401 can be waterproof to protect the electronics unit 403 from fluid within the dressing. In some embodiments, the flexible film 402 can be sized appropriately so as not to limit the flexibility of the assembly. In some embodiments, depending on the properties of the film 402, the electronics assembly 400 can be thermoformed or vacuum formed to assist in the function of maintaining the flexibility of the assembly. In some embodiments, the electronics unit 403 can be bonded or adhered to the plate 401 within the housing such that the electronics unit 403 cannot move within.

In some embodiments, the housing can include one or more windows 404. The windows 404 can be a porous film or membrane that can allow gas to pass through. The windows 404 can be a hydrophobic film or membrane. In some embodiments, the hydrophobic nature of the window 404 can repel wound fluids and prevent the leak of fluids into the electronics assembly 400. In some embodiments, the windows 404 can include a bacterial filter. In some embodiments, the windows 404 can have the porosity that enables them to act as a bacterial filter and preventing bacterial release from the body fluids into the environment. The windows 404 can also prevent the ingress of bacteria from the environment to the wound site.

The electronics assembly 400 can have more than one window 404 or a larger window 404 to provide a sufficiently large area for air movement therethrough, thus minimizing the pressure drop across the membrane and hence the power consumption of the system in achieving the pressure differential. In some embodiments, as illustrated in FIGS. 4A-4B, the electronics assembly 400 can include several windows with a small area. In other embodiments, the electronics assembly can include a window with a single large area.

The electronics assembly 400 illustrated in FIGS. 4A-4B can be incorporated within the wound dressing such that, once the dressing is applied to the body of the patient, air from within the dressing can pass through the windows 404 to be pumped out in the direction shown by the arrow on the pump 405. The exhausted air from the pump can pass out of the pump assembly through the pump exhaust mechanism 406 and be exhausted or vented from the housing of the electronics assembly 400 through an aperture or vent 408 in the plate 401. In some embodiments, the flexible circuit board 409 can be positioned between the exhaust mechanism 406 and the plate 401. The flexible circuit board 409 can also include an aperture or vent aligned with the exhaust hole in the exhaust mechanism as described with reference to FIGS. 2A-2B. The vent hole or apertures in the exhaust mechanism 406, flexible circuit board 409, and plate 401 can be aligned and sealed to each other. This seal can ensure the pump exhaust is exhausted from the electronics assembly 400 through the vent 408 in the plate 401. In other embodiments, the exhaust mechanism 406 of the electronics unit 403 can be positioned on and bonded directly to the plate 401 with an air tight seal.

The top side of the plate 401 (not shown in FIGS. 4A-4B) can include a label similar to the label described with reference to FIGS. 3A-3C. In other embodiments, the top side of the plate 401 can integrate the components of the label described with reference to FIG. 3A-3C within the plate 401. In such embodiments, a separate label is not needed. For example, in addition to the vent holes, the plate 401 can include the indicator portions and/or a switch cover described previously herein.

In some embodiments, the electronics assembly 400 can be embedded within the wound dressing in the same manner as the electronics unit described with reference to FIGS. 3A-3C. The dressing can have one or more absorbent layers within the dressing and the absorbent layers can have a single aperture or recess for receiving the electronics assembly within. In some embodiments, the electronics assembly can be positioned below the overlay layer similar to the electronics unit described with reference to FIGS. 3A-3C. In such embodiments, the overlay layer would include an aperture to allow access to at least a portion of the top surface of the plate 401.

When the electronics assembly 400 is positioned within the dressing it can be positioned below the wound cover and the overlay layer similar to the electronics unit described with reference to FIGS. 3A-3C. In other embodiments, an overlay layer is not used and the electronics assembly 400 is positioned directly below the cover layer or backing layer.

The cover layer or backing layer can include an aperture exposing a portion of, most of, or all of the top surface of the plate 401. The aperture in the cover layer can be positioned over at least a portion of the plate 401 to allow access to at least a portion of the plate 401 positioned below the cover layer. In some embodiments, the cover layer can have a plurality of apertures over one or more components of the label or top surface of the plate 401. For example, the cover layer can have apertures over the vent holes, indicator portions, and/or switch cover. In other embodiments, the cover layer can have a single aperture over the one or more components of the label or top surface of the plate 401 including but not limited to the vent holes, indicator portions, and/or switch cover.

When a separate label is used, it can be applied to the dressing and exposed portion of the plate 401 as described with reference to FIGS. 3A-3C, above or below the cover layer.

Figure 5A:
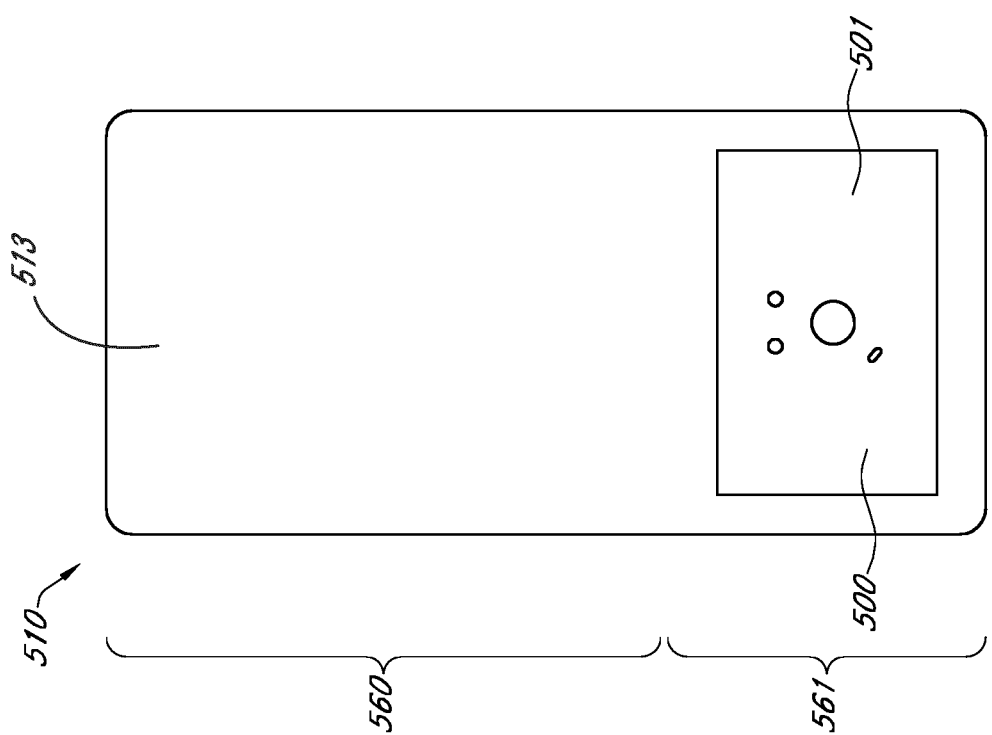
FIGS. 5A-5B illustrate embodiments of the electronics assembly positioned within an aperture in wound dressing layers.
Figure 5B:
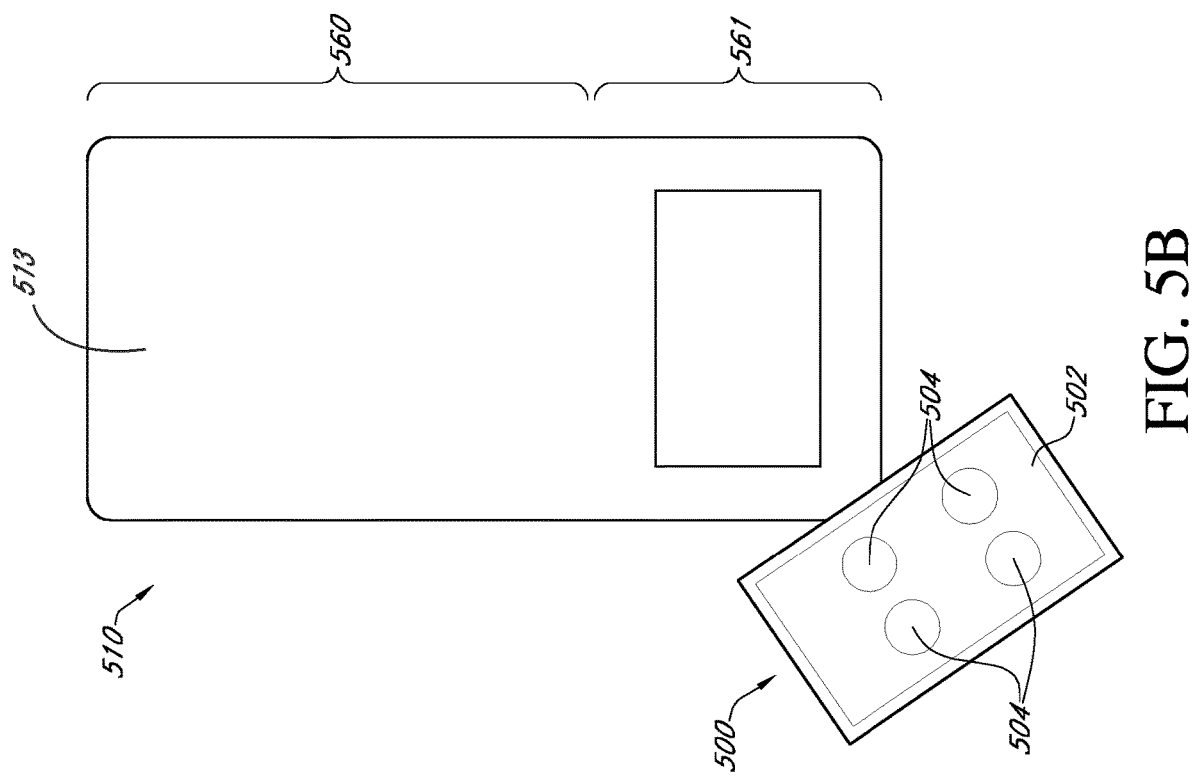

FIGS. 5A-5B illustrate embodiments of the electronics assembly 500 positioned within an aperture in wound dressing 510 layers. As illustrated in FIGS. 5A-5B, the dressing 510 can include an absorbent area 560 and an electronics area 561 similar to the corresponding components described with reference to FIGS. 1A-1C and 3A-3C. The dressing can have one or more dressing layers similar to the layers described with reference to FIGS. 1A-1C and 3A-3C. The dressing layers can have a single aperture or recess for receiving the electronics assembly within.

The wound dressing 510 can be formed from a wound contact layer, a transmission layer, and one or more absorbent layers as shown in FIGS. 1A-C and 3A-3C. The one or more absorbent layers can have a single aperture to receive the electronics assembly 500. The transmission layer and one or more absorbent materials can be covered with a cover layer 513 that seals to a perimeter of the wound contact layer as described with reference to FIGS. 1A-1C. As illustrated in FIGS. 5A-5B, the overlay layer is not used. The aperture in the one or more absorbent layers can be aligned with the aperture 520 in the cover layer 513.

FIG. 5A illustrates a top view of the electronics assembly 500 positioned in an electronics area 561 of the dressing 510. FIG. 5A illustrates a cover layer 513 of the dressing 510 with an electronics assembly 500 positioned in a recess in the dressing. The other layers of the wound dressing below the cover layer are not shown. The electronics assembly 500 can be similar to the electronics assembly described with reference to FIGS. 4A-4B. The electronics assembly 500 can include an electronics unit enclosed within a housing including a plate 501 and a flexible film 502. The plate 501 shown in FIG. 5A can include the features of the label including the one or more vents 542, one or more indicator portions 544, and/or a button or switch 543. FIG. 5B illustrates an embodiment of the electronics assembly 500 removed from the electronics area 561 of the dressing 510. The electronics assembly 500 is shown upside down with the windows facing up.

The electronics assembly can have a first side positioned on the wound facing side of the electronics assembly 500 when the dressing 510 is positioned over the wound. As illustrated, the flexible film 502 and windows 504 can form the first wound facing side of the electronics assembly 500 in contact with the dressing layer and facing the wound when the dressing is positioned over the wound. The electronics assembly 500 can have a second side opposite the first side. The plate 501 can form the second side of the electronics assembly and can be in contact with the environment when the dressing is positioned over the wound.

As illustrated in FIG. 5B, the flexible film 502 can have windows 504. When the electronics assembly 500 is positioned on or in the wound dressing as shown in FIG. 5A, the windows 504 are in fluid communication with the layers within the wound dressing allowing the electronics assembly to generate negative pressure under the dressing 510.

Figure 6:
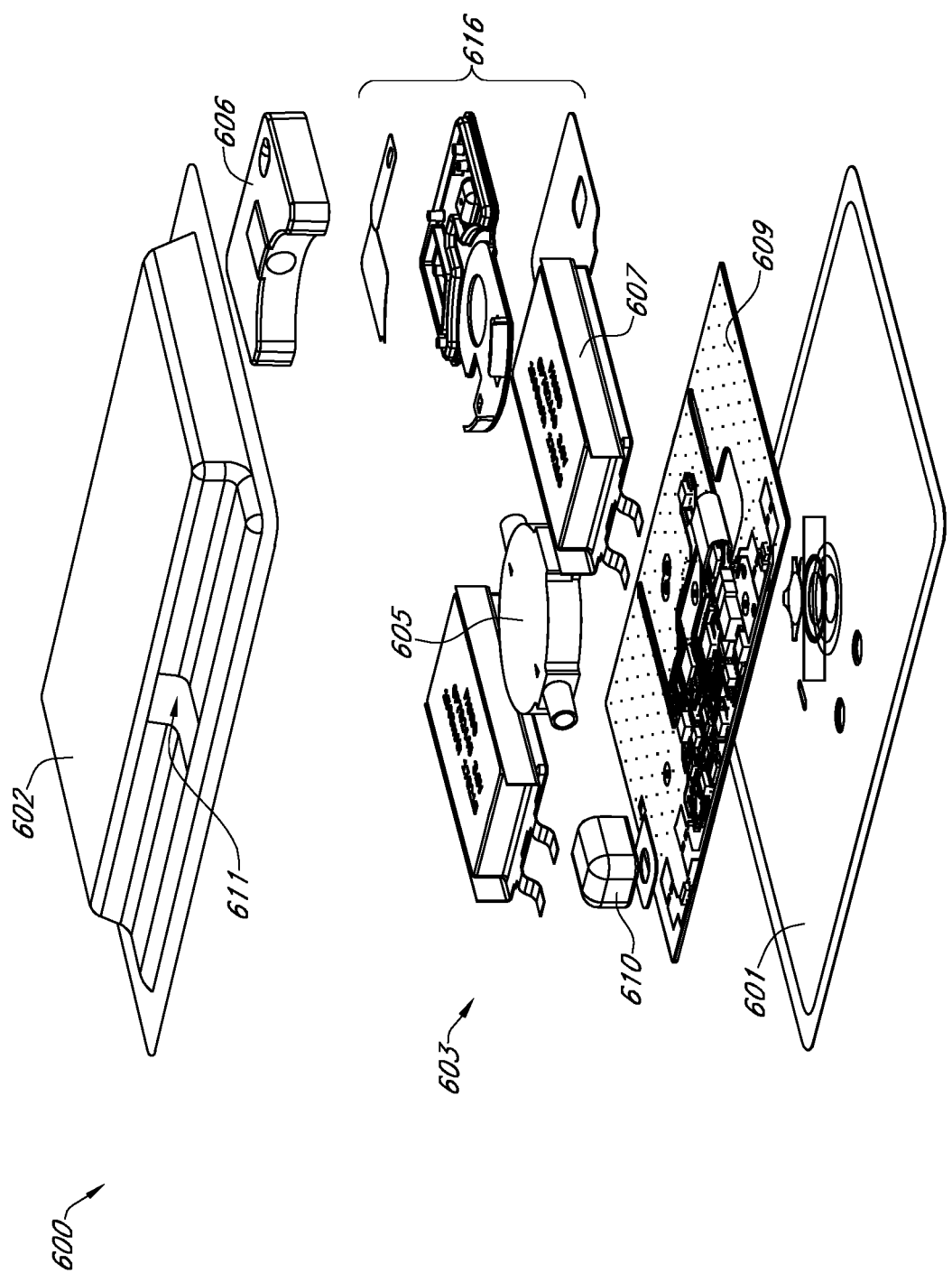
FIG. 6 is an exploded perspective view of an embodiment of an electronics assembly enclosing an electronics unit within a housing.

FIG. 6 illustrates an embodiment of an electronics assembly 600 enclosing an electronics unit within a housing. As illustrated in FIG. 6, the housing of the electronics assembly 600 can include a plate 601 and flexible film 602 enclosing the electronics unit 603 within. The electronics unit 603 can include a pump 605, inlet protection mechanism 610, pump exhaust mechanism 606, power source 607, and flexible circuit board 609.

The pump exhaust mechanism 606 can be similar to the pump exhaust mechanism 406. However, the pump exhaust mechanism 606 and the pump 605 can sit within an extended casing 616.

The flexible film 602 can be attached to the plate 601 by welding (heat welding) or adhesive bonding to form a fluid tight seal and enclosure around the electronic components. In some embodiments, the flexible film 602 can be attached to the plate at a perimeter of the plate by heat welding, adhesive bonding, ultrasonic welding, RF welding, or any other attachment or bonding technique.

The flexible film 602 can be a flexible plastic polymeric film. In some embodiments, the flexible film 602 can be formed from any material flexible polymeric film or any flexible material that confirms around the electronics. The flexible film can maintain conformability and flexibility while protecting and insulating the components within. In some embodiments, the flexible film 602 can be formed from a flexible or stretchable material, such as one or more of polyurethane, thermoplastic polyurethane (TPU), silicone, polycarbonate, polyethylene, methylated polyethylene, polyimide, polyamide, polyester, polyethelene tetraphthalate (PET), polybutalene tetreaphthalate (PBT), polyethylene naphthalate (PEN), polyetherimide (PEI), along with various fluropolymers (FEP) and copolymers, or another suitable material. In some embodiments, the flexible film 602 can be formed from polyurethane.

The plate 601 can be a plastic polymer plate. In some embodiments, the plate can be a flexible material to allow conformability to movement or flexing of the dressing when it is applied to a wound. In some embodiments, the plate can be integrated with the components of the label described with reference to FIGS. 3A-3C. In other embodiments, the label can be a separate component attached to the top surface of the plate 601. In some embodiments, the plate and/or label can have a larger surface area than the flexible circuit board and/or the electronics unit so that the flexible film 602 can seal to the outer perimeter of the plate and/or label around the flexible circuit board and/or the electronics unit.

The flexible film 602 and plate 601 can be waterproof to protect the electronics unit 603 from fluid within the dressing. In some embodiments, the flexible film 602 can be sized appropriately so as not to limit the flexibility of the assembly. In some embodiments, depending on the properties of the film 602, the electronics assembly 600 can be thermoformed or vacuum formed to assist in the function of maintaining the flexibility of the assembly. In some embodiments, the electronics unit 603 can be bonded or adhered to the plate 601 within the housing such that the electronics unit 603 cannot move within.

In some embodiments, the flexible film 603 can include an aperture 611. The aperture 611 can allow the inlet protection mechanism 610 to be in fluid communication with the absorbent and/or transmission layers of the wound dressing. The perimeter of the aperture 611 of the flexible film 603 can be sealed or attached to the inlet protection mechanism 610 by welding (heat welding) or adhesive bonding to form a fluid tight seal and enclosure around the inlet protection mechanism 610 allowing the electronic components 603 to remain protected from fluid within the dressing. In some embodiments, the flexible film 602 can be attached to the inlet protection mechanism 610 at a perimeter of the inlet protection mechanism 610 by heat welding, adhesive bonding, ultrasonic welding, RF welding, or any other attachment or bonding technique. The inlet protection mechanism 610 can prevent wound exudate or liquids from the wound and collected in the absorbent area 660 of the wound dressing from entering the pump and/or electronic components of the electronics assembly 600.

The electronics assembly 600 illustrated in FIG. 6 can be incorporated within the wound dressing such that, once the dressing is applied to the body of the patient, air from within the dressing can pass through the inlet protection mechanism 610 to be pumped out toward the pump exhaust mechanism 606 in communication with an aperture in the casing 616 and flexible circuit board 609 as described herein.

In some embodiments, the casing 616 can include an aperture or vent to allow the air exhausted from the pump exhaust mechanism 606 to pass through. The exhausted air from the pump can pass out of the pump assembly through the pump exhaust mechanism 606 and casing 616 and be exhausted or vented from the housing of the electronics assembly 600 through an aperture or vent in the plate 601. In some embodiments, the flexible circuit board 609 can be positioned between the exhaust mechanism 606 and the plate 601. The flexible circuit board 409 can also include an aperture or vent aligned with the exhaust hole in the exhaust mechanism as described with reference to FIGS. 2A-2B. The vent hole or apertures in the exhaust mechanism 606, casing 616, flexible circuit board 609, and plate 601 can be aligned and sealed to each other. This seal can ensure the pump exhaust is exhausted from the electronics assembly 600 through the vent in the plate 601. In other embodiments, the exhaust mechanism 606 of the electronics unit 603 can be positioned on and bonded directly to the plate 601 with an air tight seal.

The top side of the plate 601 (not shown in FIG. 6) can include a label similar to the label described with reference to FIGS. 3A-3C. In other embodiments, the top side of the plate 601 can integrate the components of the label described with reference to FIG. 3A-3C within the plate 601. In such embodiments, a separate label is not needed. For example, in addition to the vent holes, the plate 601 can include the indicator portions and/or a switch cover as described herein.

FIGS. 7A-7D show a lower wound facing surface of an electronics assembly 700. FIGS. 7A-7D illustrate embodiments of an electronics assembly including a pump inlet protection mechanism 710 sealed to the exterior of the flexible film 702 as described herein with reference to FIG. 6.

Figure 7A:
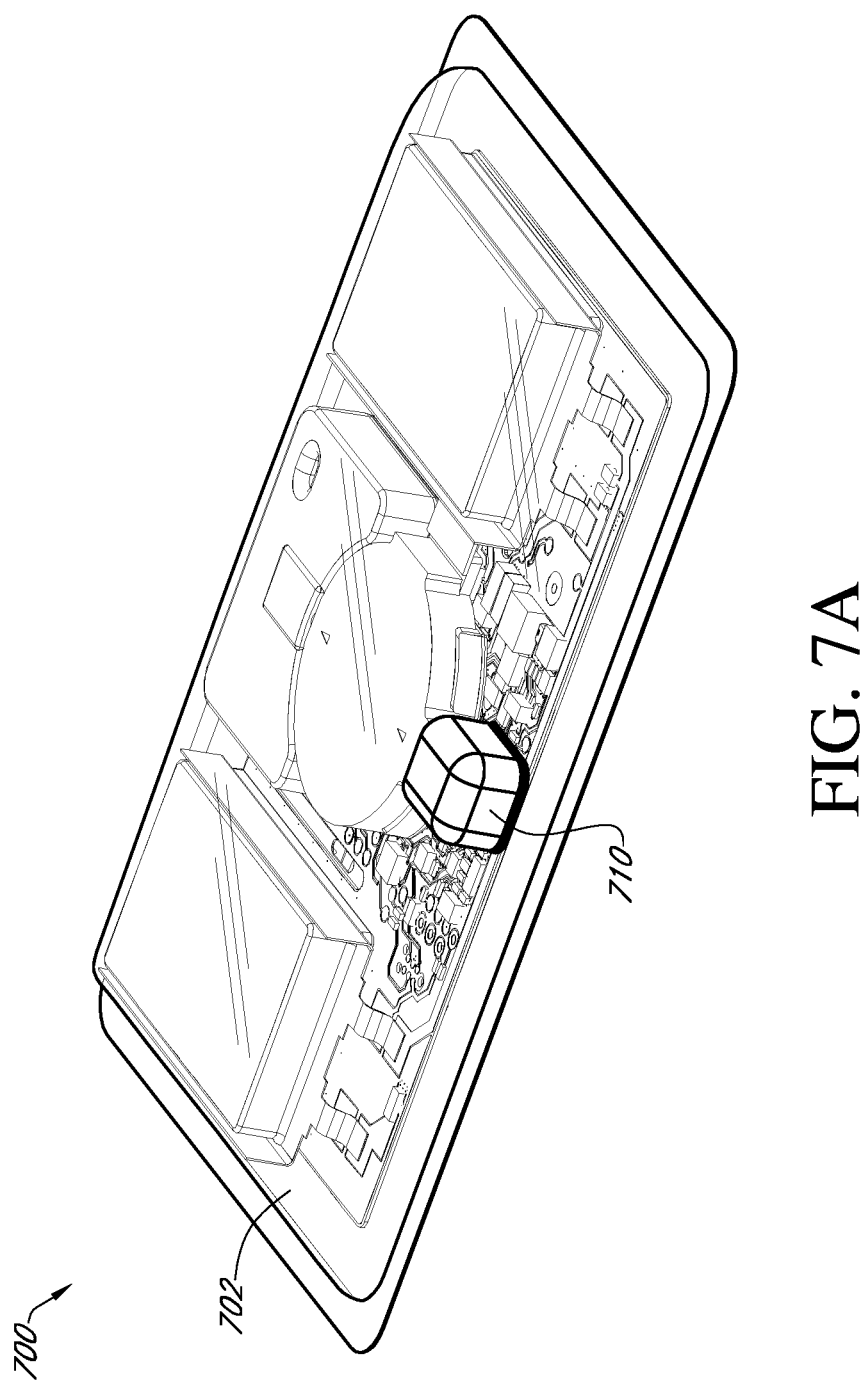
FIG. 7A illustrates a bottom perspective view of the electronics assembly of FIG. 6.
Figure 7B:
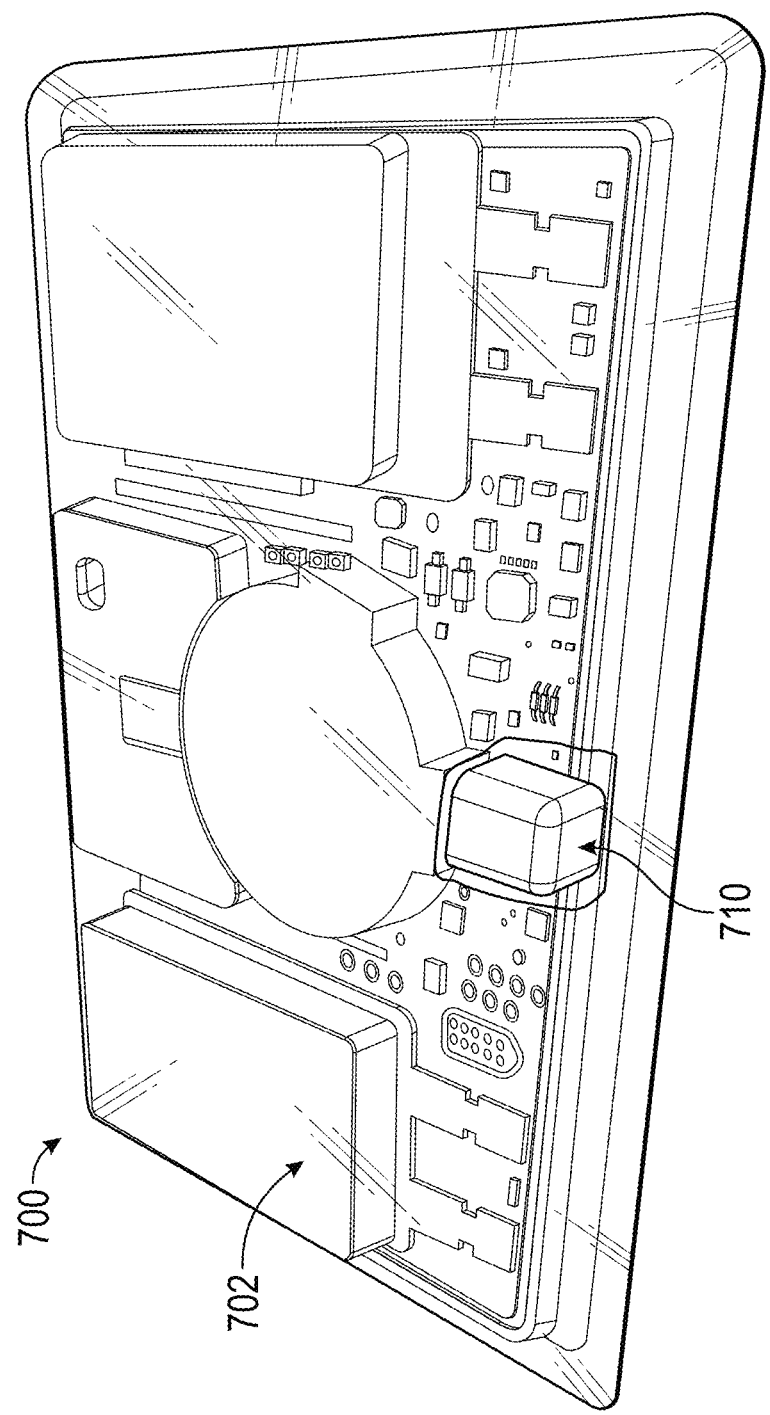
FIGS. 7B-7D show embodiments of a lower wound facing surface of an electronics assembly.
Figure 7C:
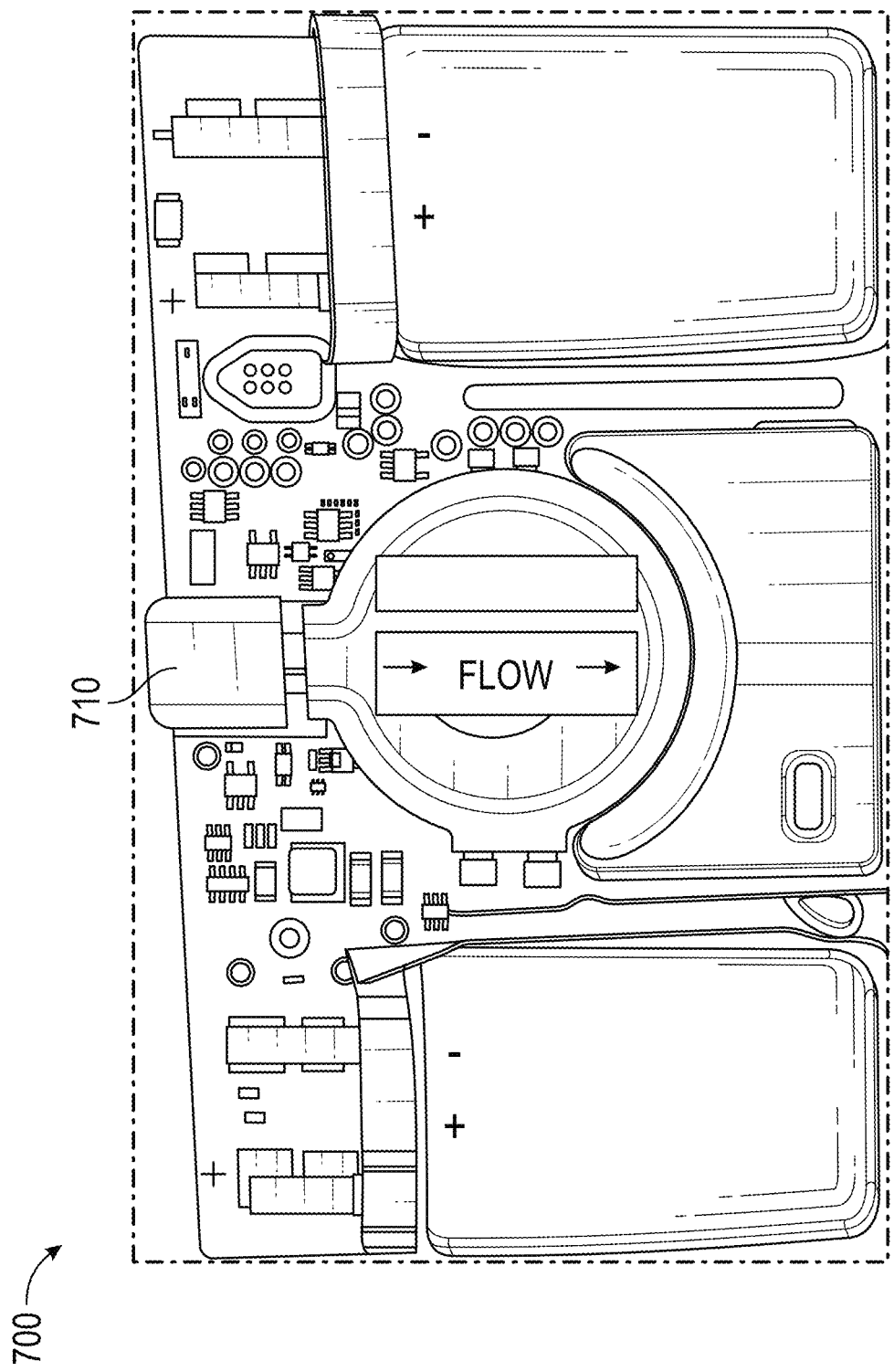
Figure 7D:
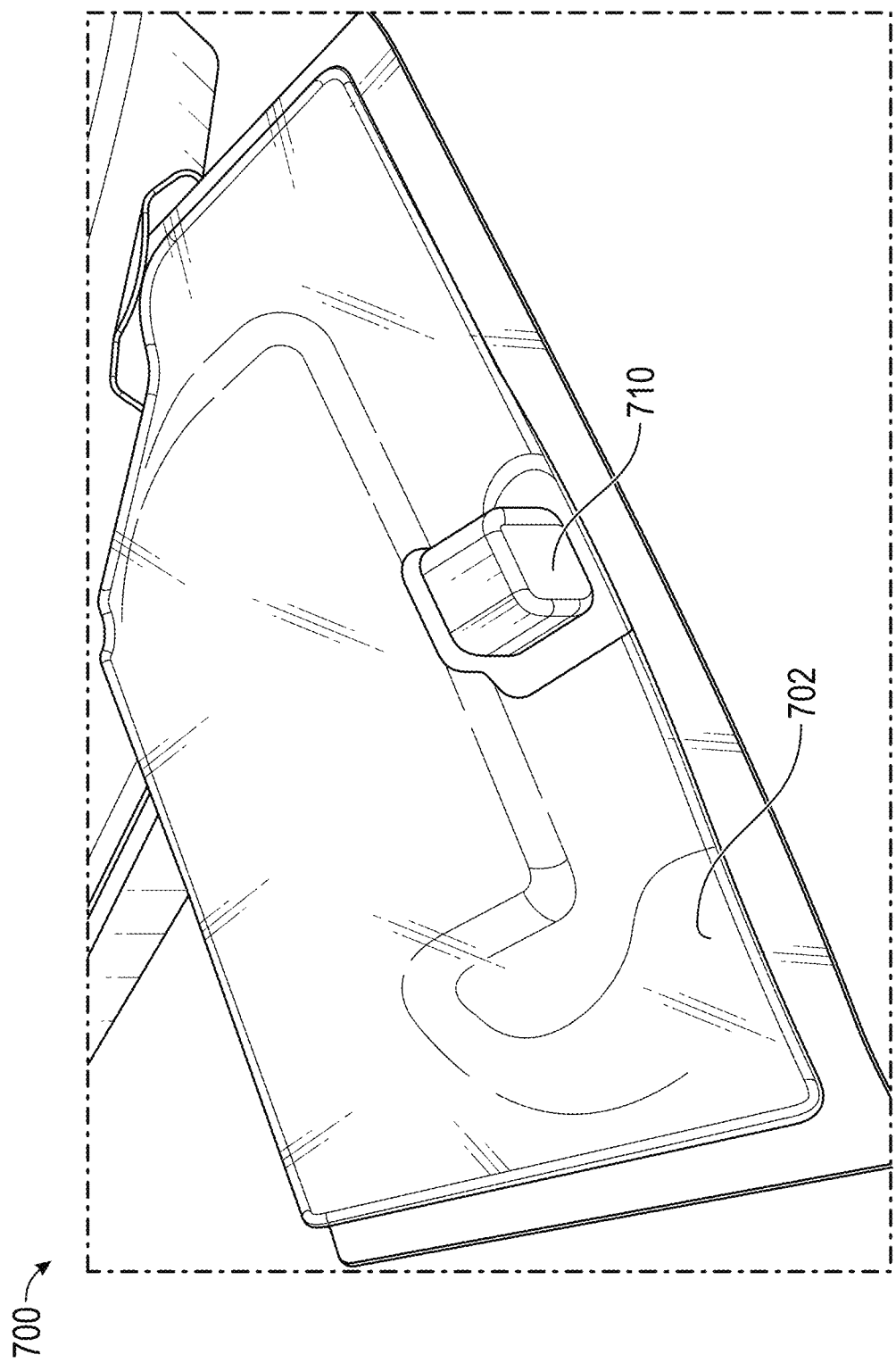
Figure 7E:
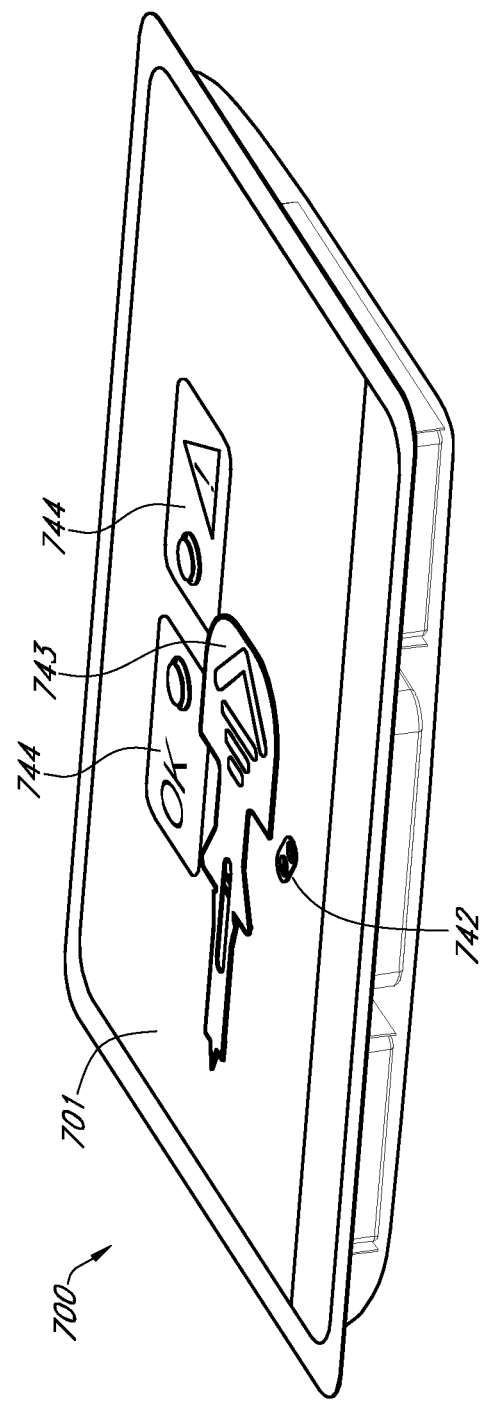
FIG. 7E illustrates a top perspective view of the electronics assembly of FIG. 6.
Figure 7F:
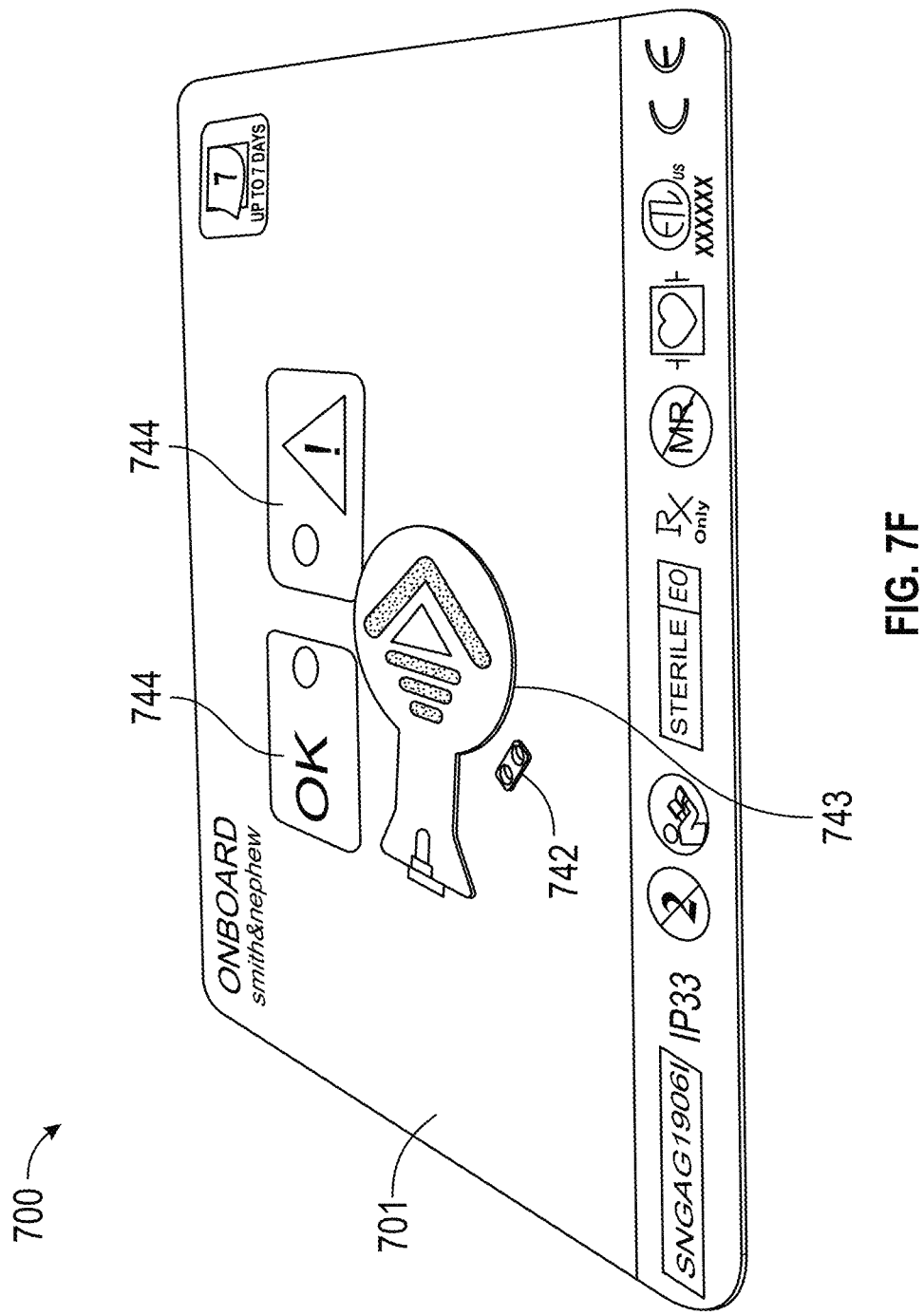
FIGS. 7F-7G show embodiments of an upper surface of an electronics assembly.
Figure 7G:
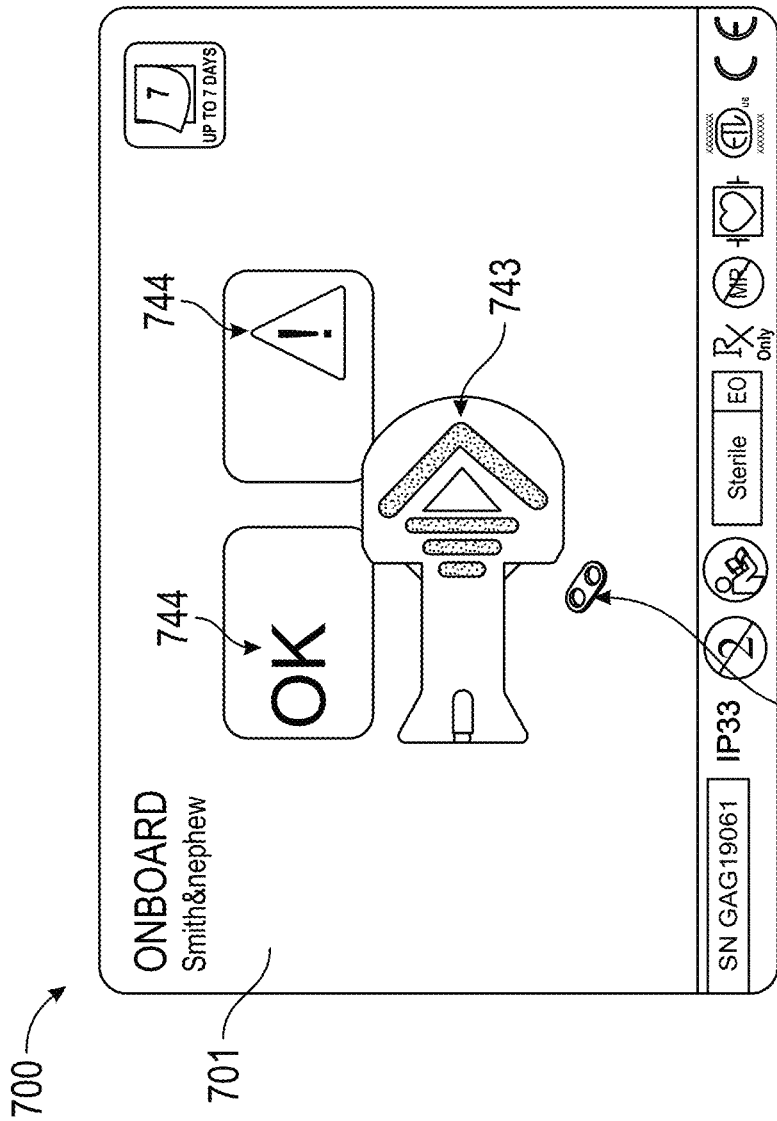

FIGS. 7E-7G show an upper surface of the plate 701 of the electronics assembly 700. The upper surface of the plate can include an on/off switch or button cover 743, indicator portions 744, and/or vent holes 742. The on/off switch cover or button 743, indicator portions 744, and/or vent holes 342 can be similar to the switch cover or button and indictor portions described with reference to FIGS. 3A-3C, 4A-4B, and 5A-5B.

In some embodiments, as shown in FIGS. 7E, 7F, and 7G, the switch or button cover 743 can be positioned over the switch on the flexible circuit board of the electronics components as described herein. In some embodiments, the plate can include embossed features for the switch cover 743. In some embodiments, the embossed features of the switch cover 743 can prevent accidental activation or deactivation of the device. In some embodiments, the switch or switch cover 743 can include a tab on the switch to prevent accidental activation or deactivation.

In some embodiments, as shown in FIGS. 7E, 7F, and 7G, the indicator portions can include visual symbols or words to indicate the condition of the wound dressing and electronics. For example, as shown in FIGS. 7E, 7F, and 7G, one indicator portion can read "OK". When the LED or light source associated with the "OK" indicator portion is illuminated the user is provided an indication that the dressing or electronics are functioning properly. An indicator portion can have a symbol, for example, a caution symbol similar to the symbol shown in FIGS. 7E-7G. When the LED or light source associated with the caution symbol on the indicator portion is illuminated the user is provided an indication that the dressing or electronics may not be functioning properly and/or there may be a leak.

The vent holes 742 of the plate can allow exhaust from the pump outlet mechanism to pass through the plate and exit the wound dressing to be exhausted to the atmosphere.

Figure 7H:
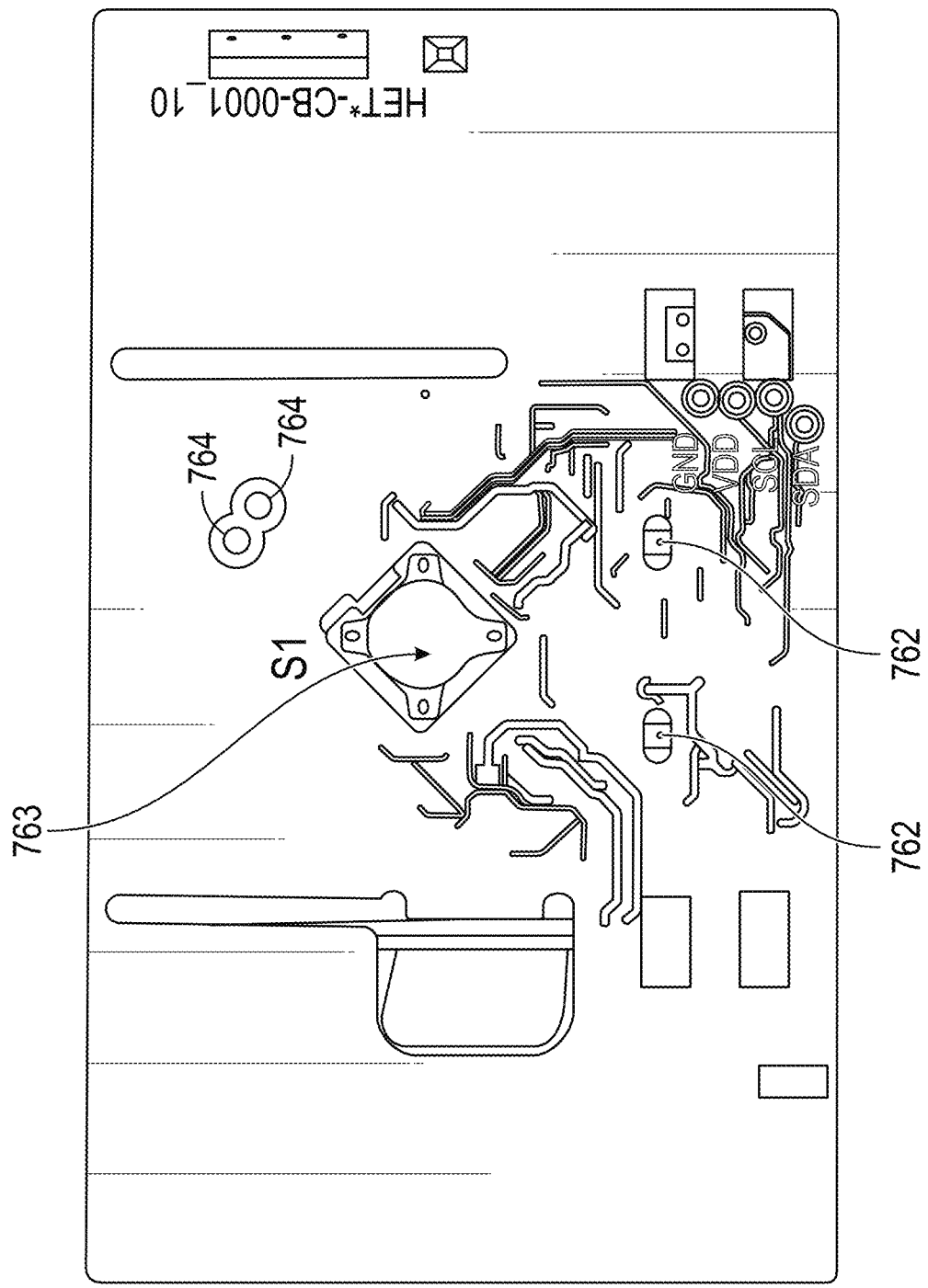
FIG. 7H illustrates an embodiment of a top surface of a flexible circuit board of the electronics unit.

FIG. 7H illustrates an embodiment of a top surface of a flexible circuit board of the electronics unit. The top surface of the flexible circuit board can include light or LED indicators 762, switch or button 763, and vent apertures 764 as illustrated in FIG. 7H and described in more detail herein.

Figure 7I:
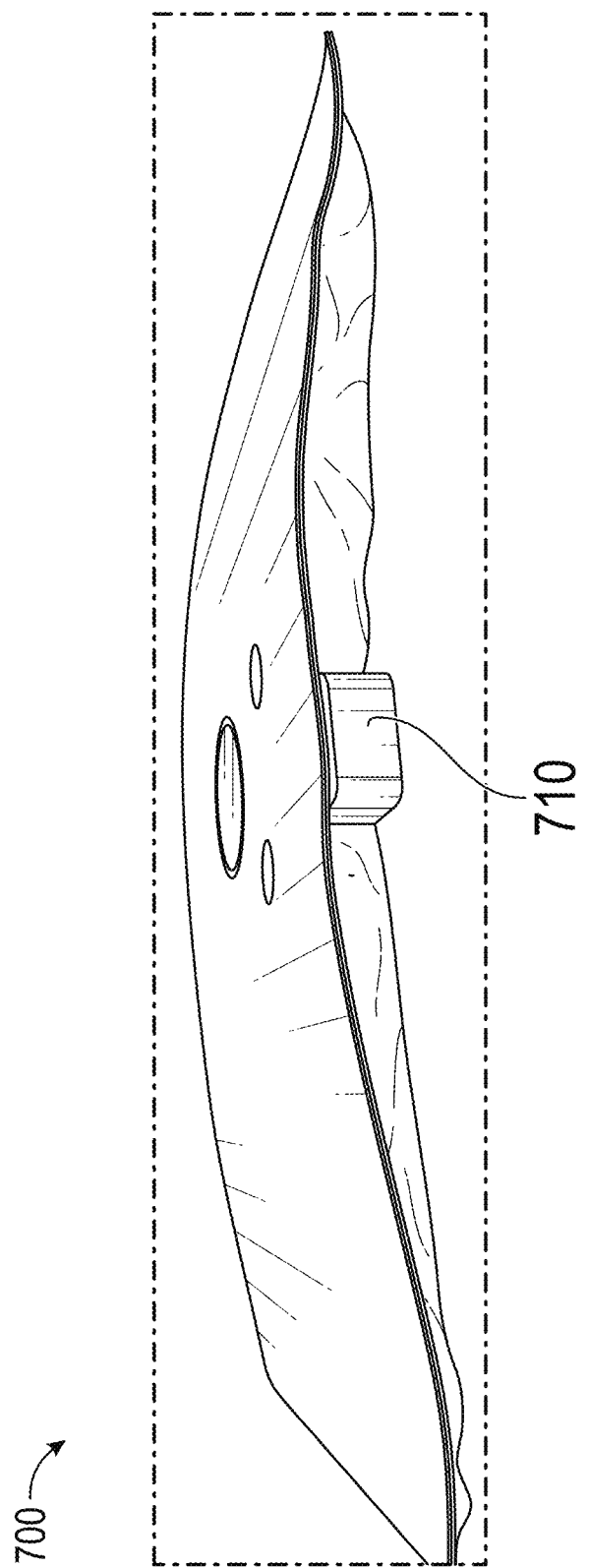
FIG. 7I illustrates a side view of an embodiment of an electronics assembly.

FIG. 7I illustrates a side view of an embodiment of the electronics assembly 700 and the pump inlet protection mechanism 710 is visible.

The electronics assembly 700 with the pump inlet protection mechanism 710 extending from and sealed to the film 702 can be positioned within the aperture 520 in the cover layer 513 and absorbent layer(s) (not shown) as shown in FIGS. 5A-5B and described in more detail herein. In some embodiments, the perimeter of the electronics assembly 700 can be sealed to a top surface of the outer perimeter of the aperture 520 in the cover layer 513 as shown in FIGS. 5A-5B and described in more detail with reference to FIGS. 9A-9B herein. In some embodiments, the electronics assembly 700 is sealed to the cover layer 513 with a sealant gasket, adhesive, heat welding, adhesive bonding, ultrasonic welding, RF welding, or any other attachment or bonding technique. In some embodiments, the electronics assembly 700 can be permanently sealed to the cover layer 513 and could not be removed from the cover layer without destroying the dressing.

In some embodiments, the electronics assembly 700 can be utilized in a single dressing and disposed of with the dressing. In other embodiments, the electronics assembly 700 can be utilized in a series of dressings.

Electronic Assembly Incorporated within the Wound Dressing

Figure 8:
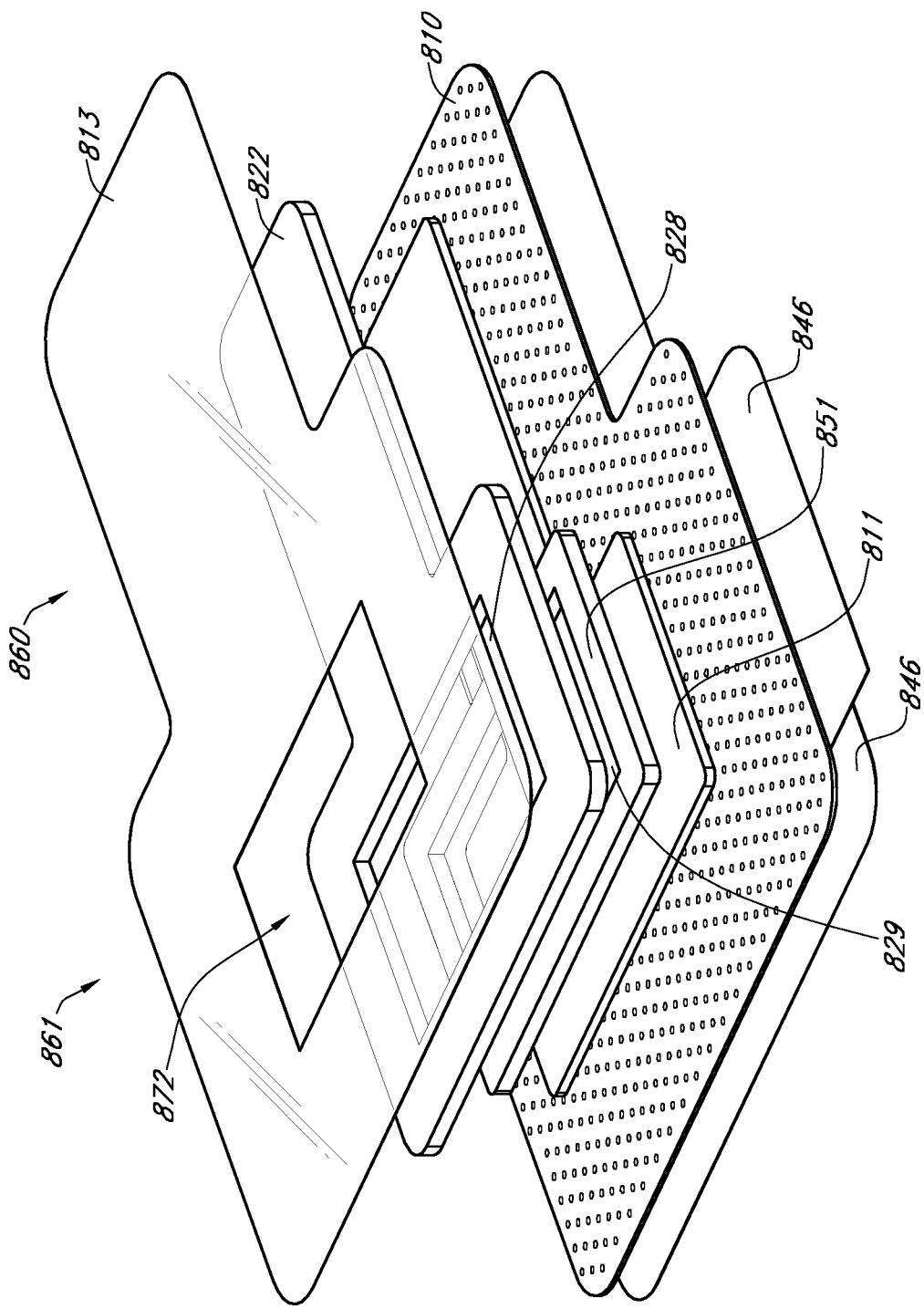
FIG. 8 illustrates an embodiment of wound dressing layers of a wound dressing for use with an electronics assembly.

FIG. 8 illustrates an embodiment of wound dressing layers for a wound dressing that can be used with the incorporates electronics components and/or electronics assembly described herein. The dressing layers and components of FIG. 8 can be similar to the dressing layers and components described in FIG. 3A. However, the wound dressing illustrated in FIG. 8 can incorporate electronic components and negative pressure source enclosed within an electronics assembly similar to the electronics assembly 400, 500, 600, and 700 described with reference to FIGS. 4A-4B, FIGS. 5A-5B, FIG. 6, and FIGS. 7A-7I. FIG. 8 illustrates a wound dressing with a wound contact layer 810 configured to contact the wound. A transmission layer or spacer layer 811 is provided over the wound contact layer. The transmission layer 811 can assist in transmitting and distributing negative pressure over the wound site.

A first layer of apertured absorbent material 851 can be provided over the transmission layer 811. The first apertured absorbent layer 851 can include one or more apertures 829.

In some embodiments, the aperture 829 can be sized and shaped to fit an electronics assembly and/or electronics unit therein. The first apertured absorbent layer 851 can be sized and shaped to the size of the electronics area 861 and does not extend into the absorbent area 860. In some embodiments, the aperture 829 can be shaped and sized to fit the electronics assembly formed from the plate and film described with reference to FIGS. 4A-7I.

A second apertured absorbent layer 822 can be provided over the first absorbent layer 851. In some embodiments, the second absorbent layer 822 includes one or more apertures 828. The second absorbent layer 822 can be sized and shaped to the size of the electronics area 861 and the absorbent area 860. In some embodiments, the aperture 828 can be shaped and sized to fit the electronics assembly formed from the plate and film described with reference to FIGS. 4A-7I.

A cover layer or backing layer 813 can be positioned over the absorbent material 822. The cover layer 813 can form a seal to the wound contact layer 810 at a perimeter region enclosing the absorbent layers 822 and 851 and the transmission layer 811. In some embodiments, the cover layer 813 can be a flexible sheet of material that forms and molds around the dressing components when they are applied to the wound. In other embodiments, the cover layer 813 can be a material that is preformed or premolded to fit around the dressing components. As used herein, the terms cover layer and backing layer can be used interchangeably to refer to the layer of material in the dressing configured to cover the layers of the wound dressing.

In some embodiments, the cover layer or backing layer 813 can include an aperture 872. The aperture 372 can be positioned over at least a portion of the aperture 828 in the absorbent layer 822 to allow access and fluid communication to at least a portion of the absorbent layers 822 and 851, transmission layer 811, and would contact layer 810 positioned below. The wound contact layer, the transmission layer, and/or the absorbent layer can be optional layers and the wound dressing can be formed without any of these layers.

An electronics assembly can be positioned in the apertures 828, 829, and 872 of the first and second absorbent material 851 and 822 and the cover layer 813. The electronics assembly can include a pump, power source, and a printed circuit board as described with reference to FIGS. 4A-5B, 6, and 7A-7I.

Before use, the dressing can include one or more delivery layers 846 adhered to the bottom surface of the wound contact layer. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Figure 9A:
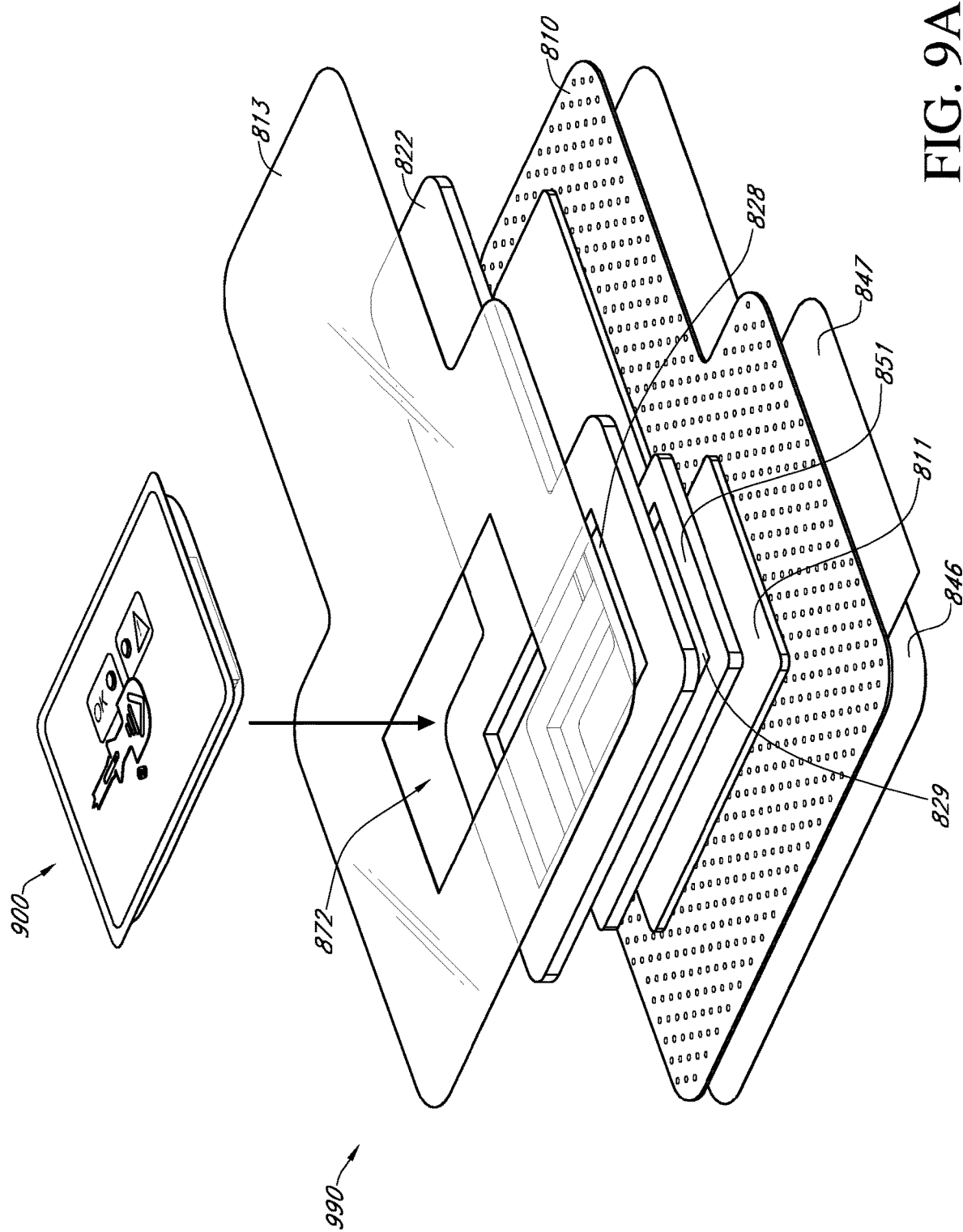
FIG. 9A illustrates an embodiment of a wound dressing incorporating an electronics assembly within the wound dressing layers.

FIG. 9A illustrates an embodiment of a wound dressing incorporating an electronics assembly 900 within the wound dressing layers 990. The electronics assembly 900 can be provided within the aperture 872 in the cover layer and apertures 829 and 828 in the first and second absorbent layers. In some embodiments, the electronics assembly 900 can seal to the outer perimeter of the aperture 872 of the cover layer.

The electronics assembly 900 can include the pump inlet protection mechanism extending from and sealed to the film as described in FIGS. 6 and 7A-7I. The electronics assembly 900 can be positioned within the apertures 872, 829, 828 in the cover layer and absorbent layer(s) as shown in FIG. 9A. In some embodiments, the perimeter of the electronics assembly 900 can be sealed to a top surface of the outer perimeter of the aperture 872 in the cover layer as shown in FIG. 9A. In some embodiments, the electronics assembly 700 is sealed to the cover layer 813 with a sealant gasket, adhesive, heat welding, adhesive bonding, ultrasonic welding, RF welding, or any other attachment or bonding technique. In some embodiments, the electronics assembly 900 can be permanently sealed to the cover layer 813 and could not be removed from the cover layer without destroying the dressing.

In some embodiments, the electronics assembly 900 can be utilized in a single dressing and disposed of with the dressing. In other embodiments, the electronics assembly 900 can be utilized or re-used (e.g., after sterilization) in a series of dressings.

Figure 9B:
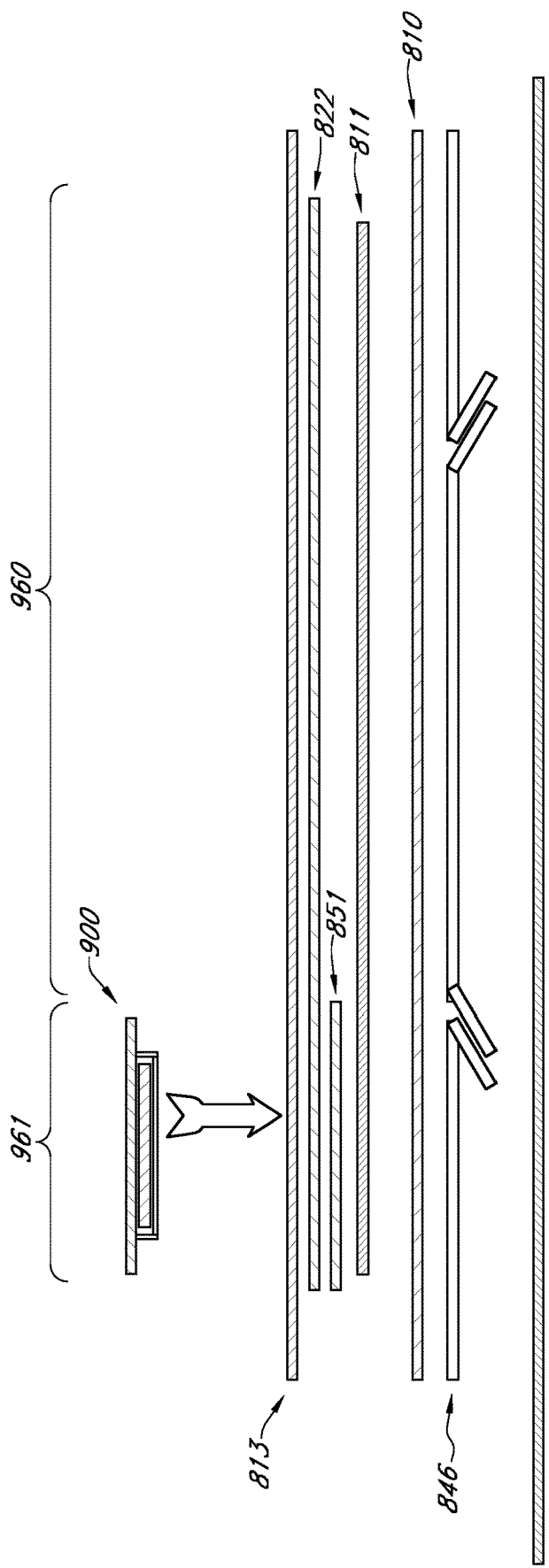
FIG. 9B illustrates a cross sectional layout of the material layers of the wound dressing incorporating an electronics assembly within the dressing.

FIG. 9B illustrates a cross sectional layout of the material layers of the wound dressing incorporating an electronics assembly within the dressing. The dressing included multiple material layers and an electronics assembly 900. The wound dressing can include an electronics area 961 including the electronics and an absorbent area or dressing area 960 that is intended to be applied to the wound as described with reference to FIGS. 1A-1C.

As described herein, the one or more material layers can extend into both the electronics area 961 and the dressing area 960. The dressing can include a wound contact layer 810, transmission layer 811, absorbent layers 822 and 851, and a cover or backing layer 813 as illustrated in FIG. 9B. The absorbent layers 822 and 851 and cover layer 813 can include recesses or cutouts to receive the components of the electronics assembly 900 as described with reference to FIG. 9A. In some embodiments, the small apertured absorbent layer 851 can be positioned on top of the large apertured absorbent layer 822. In other embodiments, as illustrated in FIGS. 9A-9B the small apertured absorbent layer 851 can be positioned below of the large apertured absorbent layer 822.

In some embodiments, the electronics assembly 900 can be inserted and affixed in the dressing layers. As illustrated in FIG. 9A, the lower wound facing face of the film enclosing the electronics assembly can be sealed directly to the upper surface of the cover layer 813 of the dressing.

Before use, the dressing can include a delivery layer 846 adhered to the bottom surface of the wound contact layer 810. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Figure 10C:
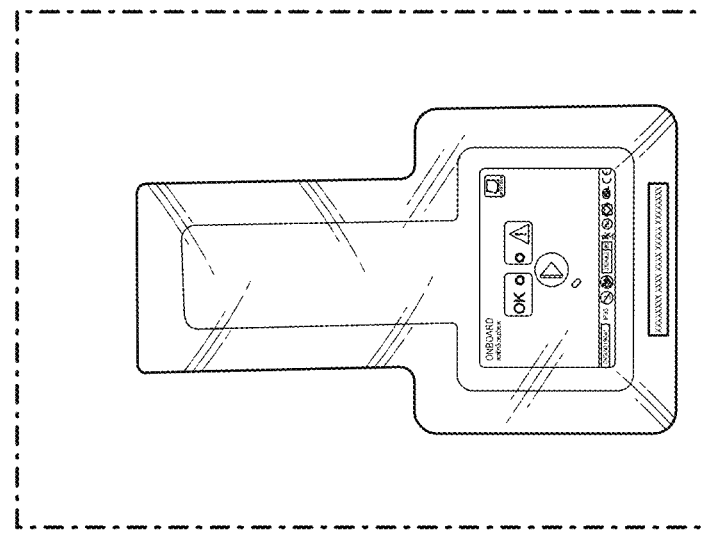
FIGS. 10A-10E illustrate embodiments of various shapes and sizes for the wound dressing incorporating an electronics assembly.
Figure 10B:
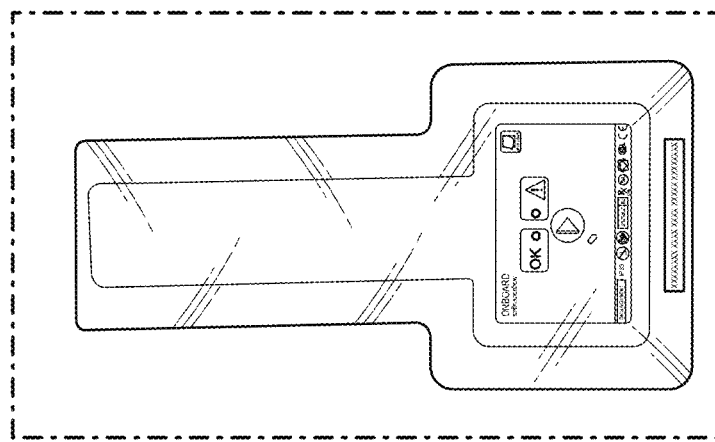
Figure 10A:
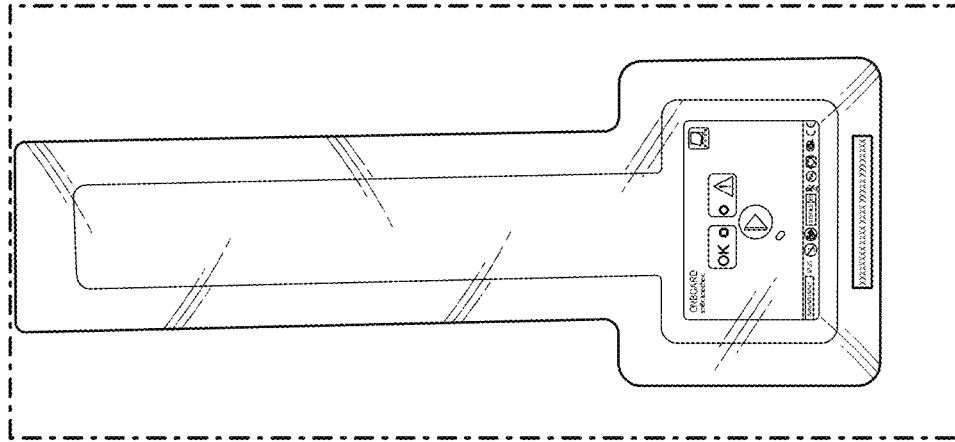
Figure 10E:
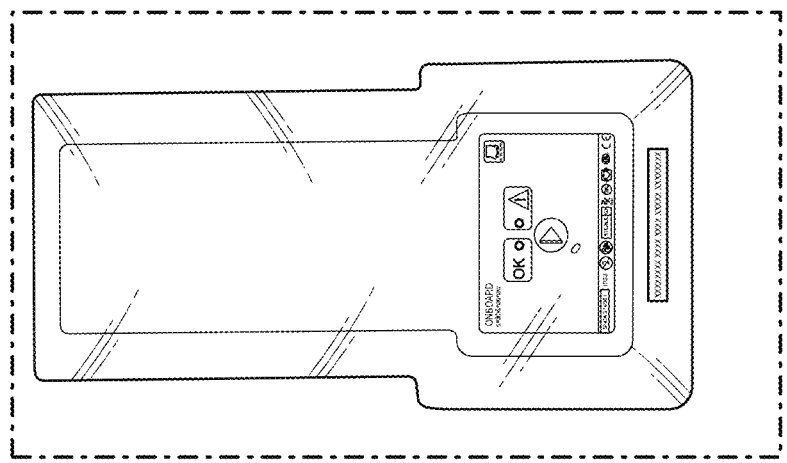
Figure 10D:
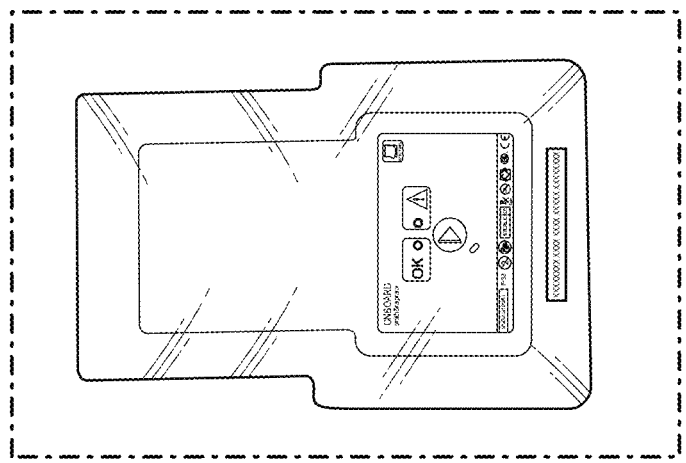

FIGS. 10A-10E illustrate embodiments of various shapes and sizes for the wound dressing incorporating an electronics assembly. The wound dressing with embedded electronics assembly can be any shape or size to accommodate various types of wounds and conform to the shapes and contours of the patient's body. For example, the wound dressing with embedded electronics can have a rectangular, rounded rectangular, square, T shaped, or any other shape or design. The wound dressing can have a longitudinal length that is parallel to a longitudinal axis that extends the length of the dressing passing through the electronics area and absorbent area. The absorbent area can have a longitudinal axis extending parallel to the longitudinal axis of the dressing. In some embodiments, the dressing has a length that is longer parallel to the longitudinal axis than it is wide. The electronics assembly can have a longitudinal axis that is perpendicular to the longitudinal axis of the absorbent area. In some embodiments, electronics assembly can have a length parallel to its longitudinal axis that is longer than it is wide. In some embodiments, the absorbent area of the wound dressing can be an elongated rectangular shape that includes a length of the absorbent area that is greater than the width of the absorbent area as illustrated in FIGS. 10A-10C, and 10E. In some embodiments, the absorbent area of the wound dressing can have a square shape that includes a length of the absorbent area that is substantially equal to or equal to the width of the absorbent area as illustrated in FIG. 10D. In some embodiments, the wound dressings with embedded electronics described herein can be rectangular or rounded rectangular shaped as illustrated with reference to FIGS. 1A-2B and 5A-5B. In other embodiments, the wound dressings with embedded electronics described herein can be a T shaped as illustrated with reference to FIGS. 3A-3C and FIGS. 8-10E.

Protective Film within Electronics Area

In some embodiments, the wound dressing as described with reference to FIGS. 8 and 9A-9B can be used with a removeable or replaceable electronics assembly. The wound dressing can incorporate an electronics unit similar to the electronics unit described with reference to FIGS. 4A-7I. However, in some embodiments, the flexible film (shown as 602 and 702 in FIG. 6 and FIGS. 7A-7I) can be incorporated into the dressing separately from the remainder of the electronics assembly. The flexible film can be placed within the apertures or openings described herein and shown as 872, 828, and 829 in FIGS. 8 and 9A within the absorbent layers and cover layer of the wound dressing. Embodiments of the wound dressings, wound treatment apparatuses and methods described herein may also be used in combination or in addition to those described in International Application No. PCT/EP2018/074701, filed Sep. 13, 2018, International Application No. PCT/EP2018/079345, filed Oct. 25, 2018, and International Application No. PCT/EP2018/074694, filed Sep. 13, 2018, and which are hereby incorporated by reference in their entirety.

In some embodiments, the film placed within the apertures or openings in the absorbent and cover layer of the wound dressing can be a flexible material or can be preformed or preshaped into a molded or structured film material before inserting the film into the wound dressing. As described herein, the terms preformed or preshaped material refers to a material that is shaped or formed or molded beforehand into a permanent or semi-permanent object. The film formed from a flexible material or preformed or preshaped into a molded or structured film material before inserting the film into the wound dressing can be referred to herein as a protective film or a film that is used to separate and protect the electronics unit from the wound exudate or liquids stored in the wound dressing including the absorbent material. The film can be sealed to the cover layer at the perimeter of the aperture or opening 872 in the cover layer 813. The film can be placed into the aperture or opening in the dressing for receiving the electronics unit. Once the film is sealed within the opening in the dressing, the film can form a cavity to receive the electronics unit. This can allow for the electronics assembly including the electronics unit and plate and/or label to be placed within the cavity in the dressing. In some embodiments, the film can be vacuumed formed to fit into the apertures or openings 872, 828, and 829 to allow for a complementary fit of the film into the apertures or openings. The electronics unit can be integrated with the plate and/or label to form an electronics assembly that can be placed within the opening. In other embodiments, the electronics unit is not integrated with the plate and/or label prior to inserting the electronics unit within the opening. In such embodiments, the electronics unit can be placed within the opening and then a plate and/or label can be placed over the electronics unit and can seal to the cover layer and/or film along the outer perimeter of the opening. Incorporating the film into the apertures or openings in the dressing can allow for the electronics unit to be replace without having to change the dressing. In some embodiments, the terms apertures or opening can be used interchangeably to refer to a cut out or hole in the material layer of the absorbent material(s) and/or the cover layer including but not limited to the apertures or openings 872, 828, and 829 described with reference to FIGS. 8-9B or similar apertures and openings in the dressing layers of the absorbent material and/or the cover layer as described herein with reference to opening 1190 in FIGS. 11A-11D described below.

The film sealed within the dressing can include a window or aperture in the film to allow the electronics unit to be in fluid communication with the absorbent layer of the wound dressing. The film can include a porous material in a window or aperture similar to the windows of porous material 404 and 504 in the flexible film described with reference to FIGS. 4A-4B and 5A-5B. In some embodiments, the porous material in the window or aperture can prevent wound exudate from entering the negative pressure source of the electronics unit. In some embodiments, a hydrophobic material can be used in the window or aperture to prevent wound exudate from entering the negative pressure source. In some embodiments, the negative pressure source can be a pump.

In some embodiments, the film sealed within the dressing can include an aperture similar to the aperture 611 shown in FIG. 6. The film can include a three-dimensional porous material in the aperture. In some embodiments, the three-dimensional porous material can be similar to the pump inlet protection mechanism 610 and 710 described with reference to FIGS. 6, 7A-7D, and 7I. The three-dimensional porous material can include a port configured to receive an inlet of a negative pressure source of the electronics unit. The port of the three-dimensional porous material can include a complementary fit with the inlet of the negative pressure source. The three-dimensional porous material is configured to prevent wound exudate from entering the negative pressure source. In some embodiments, the three-dimensional porous material can have a plug in type of connection with the inlet of the negative pressure source of the electronics unit. The port of the three-dimensional porous material can receive the inlet of the negative pressure source in a complementary fit or friction fit engagement. As used herein the terms aperture and window can be used interchangeable to refer to the aperture or hole in the film that provides fluid communication between the electronics unit and the absorbent material, transmission layer, and/or wound contact layer of the dressing.

Figure 11A:
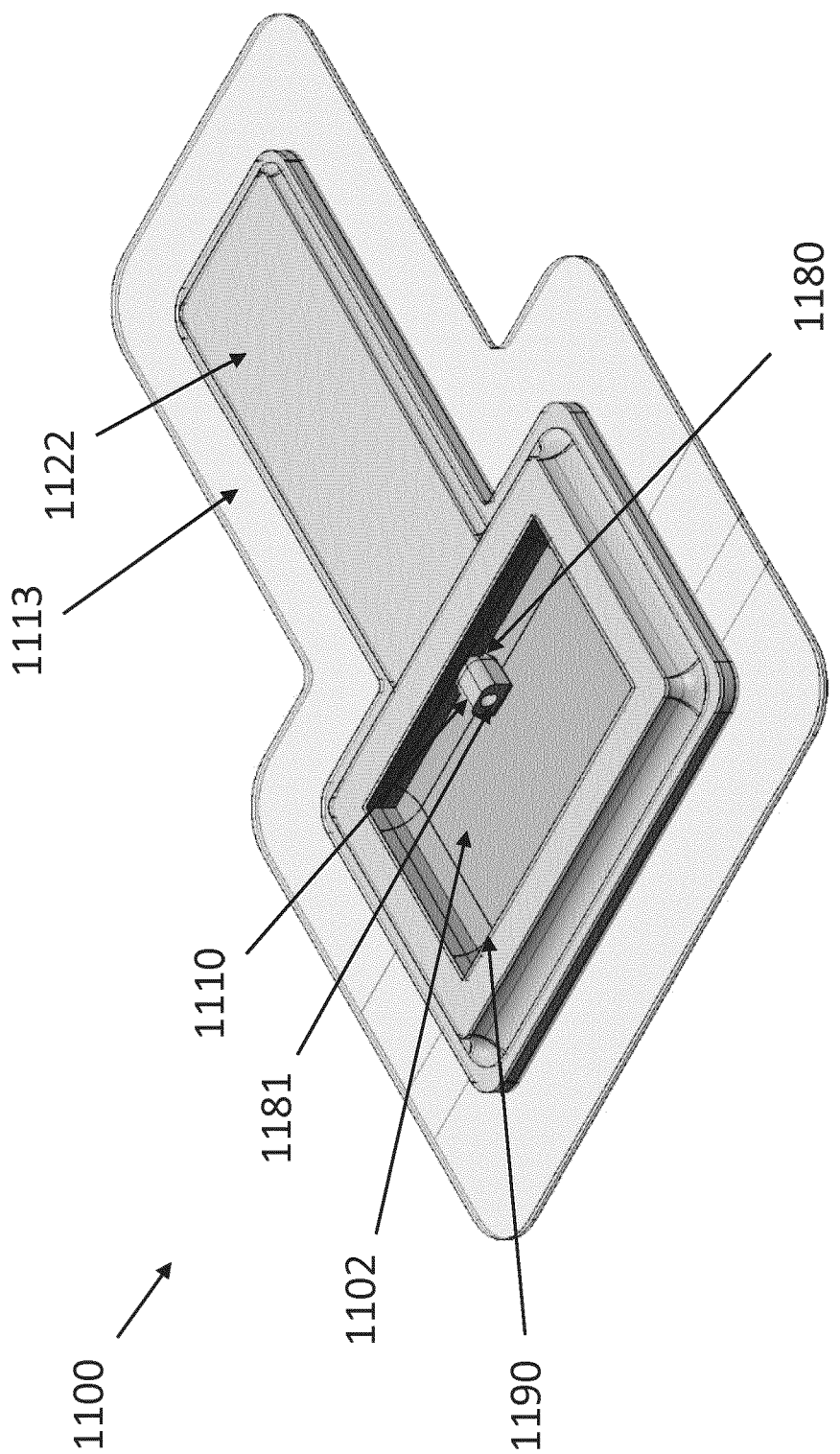
FIGS. 11A-11D illustrate embodiments of the wound dressing for incorporating integrated electronics in a vacuum formed film.
Figure 11B:
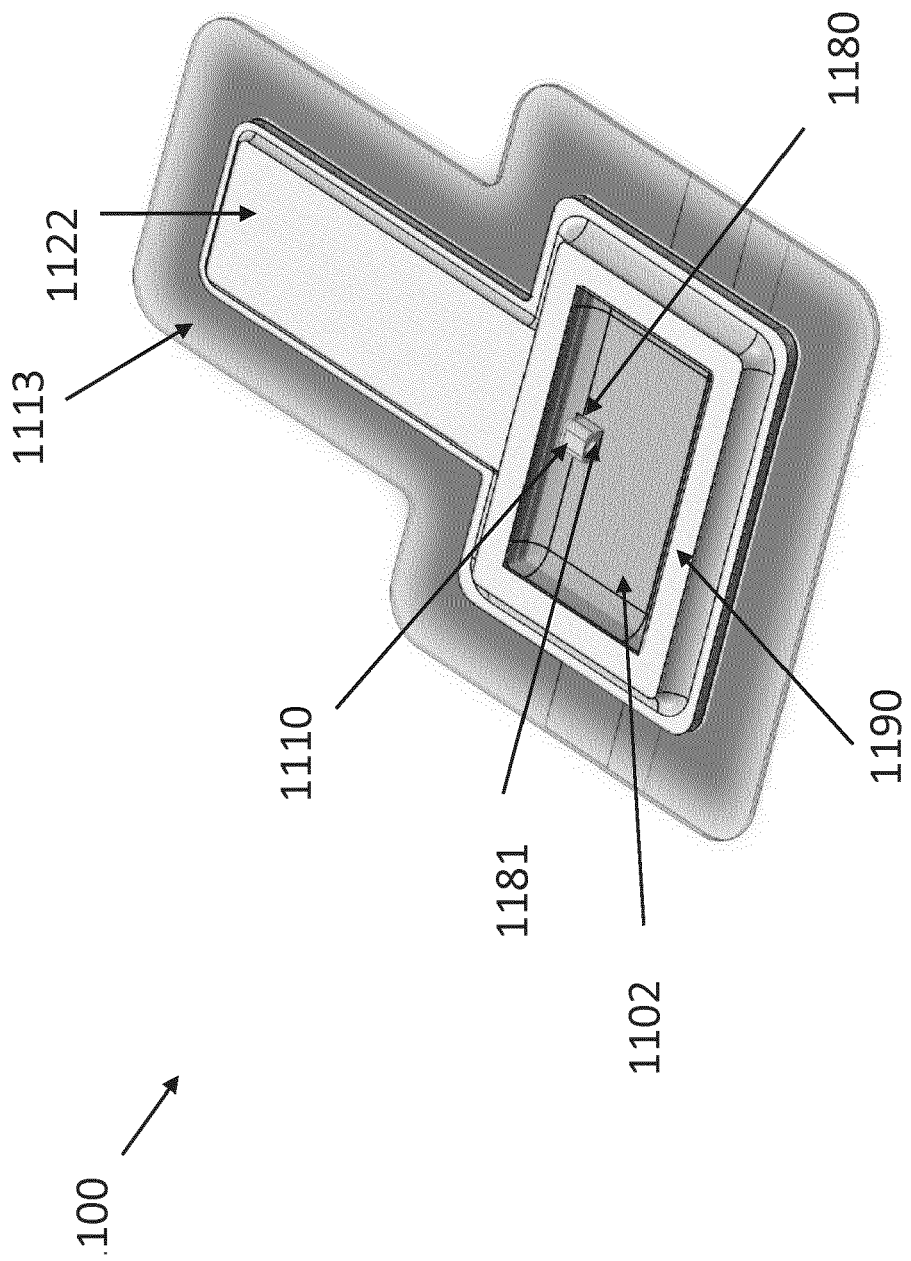

FIGS. 11A-11D illustrate embodiments of the wound dressing with an opening for incorporating integrated electronics over a film placed within the opening. In some embodiments, the film can be a vacuum formed film. In some embodiments, the film can be a thermoformed film. FIGS. 11A-D illustrate a wound dressing including a wound contact layer (not shown), a transmission layer (not shown), one or more absorbent layers 1122, and/or a cover layer 1113. These dressing layers can be similar to the wound dressing layers described with reference to FIGS. 1-10E. FIGS. 11A-11B illustrate top perspective views of the wound dressing 1100 with a film 1102 sealed within an opening 1190 of the wound dressing 1100.

The film 1102 can include one or more apertures or windows 1180. As described herein, the wound dressing can include a porous material within the one or more apertures or windows 1180. In some embodiments, the porous material can be similar to one or more filters or porous materials described within the windows described with reference to FIGS. 4A-5B. In other embodiments, the porous material can be similar to the inlet protection mechanism 610, 710 positioned in the aperture of the flexible film as described with reference to FIGS. 6-7I.

As illustrated in FIGS. 11A-11B, the wound dressing can include a three-dimensional porous material 1110 positioned within the aperture 1180 of the film 1102 similar to the inlet protection mechanism 610, 710 described with reference to FIGS. 6-7I. The three-dimensional porous material 1110 can include a port 1181. The three-dimensional porous material 1110 can be formed to cover a pump inlet of the negative pressure source or pump once the electronics assembly is inserted within the opening 1190 of the wound dressing 1100. In some embodiments, similar to the inlet protection mechanism described here, the inlet of the pump can be adhered to the three-dimensional porous material 1110. The pump inlet can be covered or fitted with the three-dimensional porous material 1110. In some embodiments, the pump inlet of a negative pressure source can be pushed onto the three-dimensional porous material 1110 illustrated in FIGS. 11A-11B. This can be a friction fit. The port 1181 of the three-dimensional porous material 1110 that receives a portion of the pump inlet can be sized and shaped to be a complementary fit around the pump inlet. In some embodiments, the three-dimensional porous material 1110 can be bonded onto the pump inlet using a silicone sealant or any other sealant or sealing technique.

In some embodiments, as described in International Application No. PCT/EP2017/059883, filed Mar. 26, 2017 and International Application No. PCT/EP2018/074694, filed Sep. 13, 2018, the disclosures of which are hereby incorporated by reference in their entireties, the three-dimensional porous material 1110 can include a cavity (not shown) that would fit around one or more sensors or other feature on the printed circuit board, when the three-dimensional porous material 1110 is in contact with the surface of a printed circuit board of the electronics unit. The pressure sensor can be used in combination with an outlet pressure sensor in communication with the outlet of the negative pressure source or pump and these pressure sensors can be used to measure and monitor the pressure levels produced by the pump as well as the pressure differential between the atmospheric pressure and the pressure underneath the wound dressing. In some embodiments, a pressure sensor can be used to monitor pressure underneath the wound dressing, such as pressure in a fluid flow path connecting the negative pressure source or pump and the wound, pressure at the wound, or pressure in the negative pressure source. In some embodiments, the pressure sensor can be in fluid communication with the cavity of the three-dimensional porous material 1110.

The three-dimensional porous material can provide a large surface area available for vacuum to be drawn by the inlet of the pump. The pump inlet can fit within the port 1181 in the three-dimensional porous material 1110. The pump inlet can be friction fit and/or form a complementary fit with the port 1181 of the three-dimensional porous material 1110 as described herein. The three-dimensional porous material can have a rounded beveled shape or any other shape. The three-dimensional porous material can be formed from a porous material that allows for air or gas to pass through and can comprise one or more porous polymer molded components. In some embodiments, the three-dimensional porous material can be hydrophobic. In some embodiments, the three-dimensional porous material can have a pore size in the range of approximately 5 microns to approximately 40 microns. In some embodiments, the pore size can be approximately 10 microns. In some embodiments, the polymer can be one of hydrophobic polyethylene or hydrophobic polypropylene. In some embodiments, the three-dimensional porous material can be formed from a Porvair Vyon material with a pore size of 10 microns.

The one or more porous polymer components can have a three-dimensional shape. For example, the one or more porous polymer components of the three-dimensional porous material can be crescent-shaped, thimble-shaped, or cuboid or generally cuboid shaped. The one or more porous polymer components of the three-dimensional porous material can also have curved or beveled corners and/or edges. The one or more porous polymer components of the three-dimensional porous material can be configured to attach to at least one of the inlet and an end of a tubular extension in fluid communication with the inlet and the interior of the wound dressing.

In some embodiments, the three-dimensional porous material 1110 can have a 3-dimensional shape and circumferentially surrounds the pump inlet when the electronics assembly is inserted within the opening 1190 covered by the film 1102 and the pump inlet is inserted within the port 1181 of the three-dimensional porous material 1110. The 3-dimensional shaped three-dimensional porous material 1110 can have a width, height, and/or length dimension that is greater than the width, height, and/or length of the pump inlet of the negative pressure source or pump. In some embodiments, the three-dimensional porous material 1110 can be a cuboid or generally cuboid shape as shown in FIGS. 11A-11D. For example, the three-dimensional porous material 1110 may have a flat negative pressure source-facing surface through which the port 1181 extends, with one or more beveled edges and/or corners.

In some embodiments, the three-dimensional porous material 1110 can circumferentially surround the pump inlet when the pump inlet is inserted into the port 1181 of the three-dimensional porous material 1110. By circumferentially surrounding the pump inlet, the three-dimensional porous material 1110 can provide a surface area larger than the surface area available at the pump inlet. The larger surface area can provide a plurality of flow paths within the three-dimensional porous material 1110. This can allow air to be drawn through a portion of the three-dimensional porous material 1110 even when another portion of the three-dimensional porous material 1110 is surrounded by fluid or otherwise blocked.

Figures 11C, 11D:
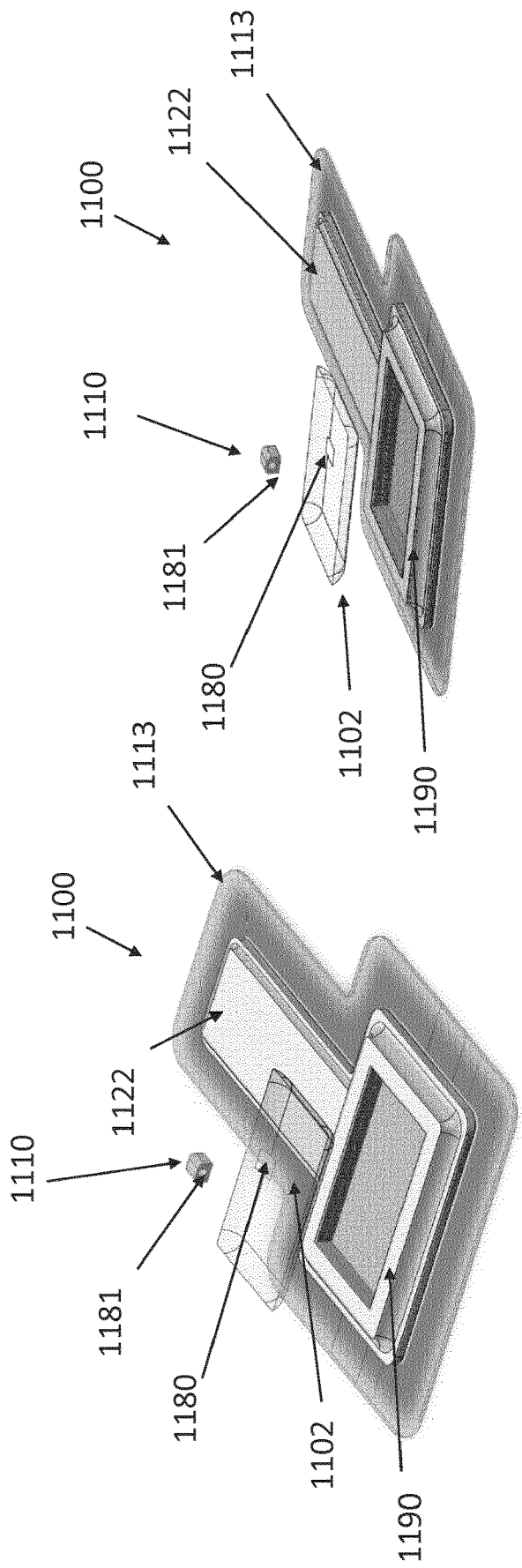

FIGS. 11C and 11D illustrate an exploded view of the wound dressing 1100, the film 1102, and the three-dimensional porous material 1110. The wound dressing 1100 can include the wound contact layer (not shown), transmission layer (not shown), absorbent layer 1122, and/or cover layer 1113. The absorbent layer 1122 can be positioned below the cover layer 1113 but can be visible through the transparent material of the cover layer 1113 as illustrated in FIGS. 11A-11D. In some embodiments, a second absorbent layer (not shown) can be used and provided in the electronics area with an aperture or opening for inserting the electronics assembly as described herein with reference to the absorbent layer 851 shown in FIGS. 8-9B. The film 1102 can be placed within an aperture or opening 1190 in the cover layer and/or the one or more absorbent layers of the wound dressing prior to insertion of the electronics assembly and/or electronics unit within the dressing. In some embodiments, the film 1102 can be preshaped for insertion into the aperture or opening 1190 of the dressing and can be sealed to the dressing. In some embodiments, the film 1102 can be thermoformed for insertion into the aperture or opening 1190 of the dressing and can be sealed to the dressing. The film 1102 can be vacuum formed for insertion within the aperture or opening 1190 of the cover layer and/or absorbent layers. The preshaped film 1102 can provide for a secure, complementary, and/or formed fit of the film 1102 within the aperture or opening 1190 in the wound dressing. The preshaped film 1102 can formed to fit within the aperture or opening 1190 of the wound dressing. The preshaped film 1102 can form a cavity to receive the electronics unit, including the negative pressure source or pump.

The vacuum formed film 1102 can formed to fit within the aperture or opening 1190 of the wound dressing with a vacuum forming technique. Vacuum forming of the film 102 can be a version of thermoforming. In some embodiments, the film 1102 can be vacuum formed using a mold that can form the film into the size and shape of the aperture or opening 1190 of the dressing. In some embodiments, the plastic, polymer, or other material of the film 1102 can be heated to a forming temperature, stretched onto a single-surface mold, and forced against the mold by a vacuum. This process can be used to form the film material into a permanent object. In some embodiments, features can be present in the design of the mold to ease removal of the formed part from the mold. In other embodiments, the film can be vacuum formed into the aperture or opening 1190 by using a vacuum placed under the dressing material.

In some embodiments, the formable sheet of the film can be mechanically or pneumatically stretched prior to bringing it into contact with the mold surface and applying the vacuum. In some embodiments, the sheet of film can be molded around a wood, structural foam, or cast or machined aluminum mold.

In some embodiments, other aspects of the electronic assembly can be preformed or preshaped. In some embodiments, the top portion of the electronics assembly including the plate and/or label can be molded or shaped. In some embodiments, the plate and/or label can be molded or shaped to accommodate features on the electronics unit. For example, the plate and/or label can be shaped to cover a protruding or raised component in the electronics unit or on the plate. In some embodiments, the components of the switch or button and/or the indicators (for example, LED indicators) could protrude from the surrounding top surface of the printed circuit board and the preshaped plate and/or label can be shaped to fit over the protruding component.

In some embodiments, the material of the electronics assembly including the film material and/or the plate or label material can be a fireproof and/or intrinsically insulating material.

Indicia or Markings on the Electronics Label

Figure 12:
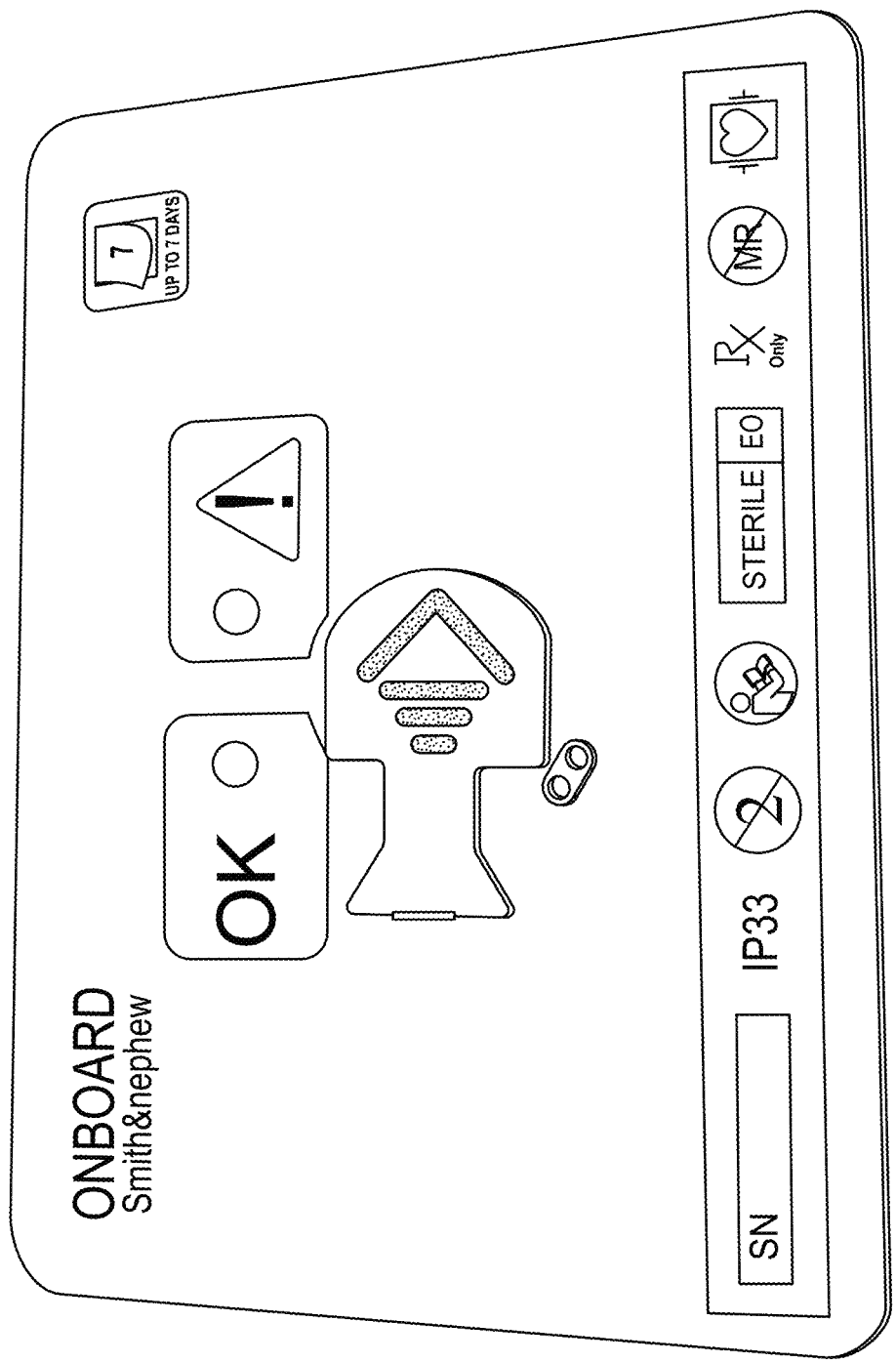
FIG. 12 illustrates an embodiment of a label of the electronics assembly including indicia or markings on the label.

In some embodiments, the label of the electronics assembly described herein with reference to FIGS. 4A-10D can include markings or indicia, for example, indicator indicia, power button or switch indicia, indicia providing user instructions, warning or use information, and/or government and regulatory indicia. FIG. 12 illustrates an embodiment of a label for an electronics assembly for use in a wound dressing. As illustrated in FIG. 12, the indicia can be visible from the top surface of the device so that it is visible by the user when the electronics assembly is placed within the wound dressing. The indicia or markings can be printed on the label. In some embodiments, the indicia or markings can be screen printed on the label. The indicia or markings can be printed on the top surface of the label (the side of the label facing away from the wound or patient's skin when the dressing is applied over a wound) and/or the bottom surface of the label (the side of the label facing the wound or patient's skin when the dressing is applied over a wound). When the indicia is printed on the bottom surface of the label, the label can be made of a transparent or substantially transparent material that allows the indicia or markings to be seen by the user on the top side of the label.

In some embodiments, the ink for the indicia and markings can be provided on the bottom surface of the label to protect the ink from being worn or rubbed off due to testing and use. For example, use of the dressing or regulatory testing for electrical safety may require the ink associated with indicia or markings on the wound dressing to be durable. For example, during use or prior to use, the label can be rubbed across its top surface or passed over on its top surface with various chemicals, however, the ink for the indicia or markings can remain intact because they are applied on the opposite surface of the label material.

The ink can be printed onto the bottom surface of a transparent material of the label and the label can be placed onto the top surface of a printed circuit board of the electronic unit as described herein. In some embodiments, the label can be attached to the printed circuit board of the electronics unit with an adhesive material and/or a double sided tape material. In some embodiments, the ink applied to the bottom surface of the label can be a UV curable material or an adhesive material and can be used to secure the bottom surface of the label to the top surface of the printed circuit board. In such embodiments, the ink can serve as the adhesive to adhere the label to the plate and no other adhesive is used. In some embodiments, the bottom surface of the label can be adhered to the top surface of the printed circuit board with a pressure sensitive adhesive, heat curable adhesive, UV curable adhesive, or any other adhesive.

In other embodiments, the ink for the indicia or markings can be applied to the top surface of the label or top surface of the printed circuit board and a film or protective covering can be placed over the ink to protect the ink from rubbing or wear during use or testing.

All of the features disclosed in this specification (including any accompanying exhibits, claims, abstract and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A wound dressing apparatus comprising:
    a wound contact layer comprising a proximal wound-facing face and a distal face, wherein the proximal wound-facing face is configured to be positioned in contact with a wound;
    at least one absorbent layer over the wound contact layer;
    a cover layer configured to cover and form a seal over the wound contact layer and the at least one absorbent layer;
    an electronics assembly comprising:
        an electronics unit comprising a negative pressure source; and
        a plate or label;
        wherein the cover layer comprises at least one opening configured to receive the electronics assembly; and
    a preshaped film, wherein the film is formed to be inserted into the at least one opening, wherein the film is configured to be inserted into the at least one opening separately from the electronic assembly;
    wherein the film comprises an aperture and the at least one absorbent layer is configured to be in fluid communication with the aperture;
    wherein the electronics assembly is configured to be placed over the film in the at least one opening and the electronics unit is enclosed within the film and the plate or label.

2. The wound dressing apparatus of claim 1, wherein the preshaped film is thermoformed.

3. The wound dressing apparatus of claim 1, wherein the preshaped film is vacuum formed.

4. The wound dressing apparatus of claim 1, wherein the at least one absorbent layer comprises at least one opening configured to receive the electronics assembly.

5. The wound dressing apparatus of claim 1, wherein the apparatus comprises a porous material in the aperture of the film, wherein the porous material is configured to prevent wound exudate from entering the negative pressure source.

6. The wound dressing apparatus of claim 1, wherein the apparatus comprises a hydrophobic material in the aperture configured to prevent wound exudate from entering the negative pressure source.

7. The wound dressing apparatus of claim 1, wherein the aperture comprises a bacterial filter.

8. The wound dressing apparatus of claim 1, wherein the apparatus comprises a three-dimensional porous material in the aperture, wherein the three-dimensional porous material is configured to receive an inlet of the negative pressure source, wherein the three-dimensional porous material is configured to prevent wound exudate from entering the negative pressure source.

9. The wound dressing apparatus of claim 8, wherein the three-dimensional porous material is sealed to the aperture in the film.

10. The wound dressing apparatus of claim 8, wherein the three-dimensional porous material comprises a port configured to receive the inlet of the negative pressure source in a complementary fit or friction fit engagement.

11. The wound dressing apparatus of claim 10, wherein the three-dimensional porous material comprises a flat negative pressure source-facing surface through which the port extends and one or more beveled edges and/or corners.

12. The wound dressing apparatus of claim 8, wherein the three-dimensional porous material circumferentially surrounds the inlet of the negative pressure source.

13. The wound dressing apparatus of claim 8, wherein the three-dimensional porous material comprises a width, height, and/or length dimension that is greater than the width, height, and/or length of the inlet of the negative pressure source.

14. The wound dressing apparatus of claim 8, wherein the three-dimensional porous material comprises a cuboid or generally cuboid shape.

15. The wound dressing apparatus of claim 1, wherein the wound dressing further comprises a transmission layer comprising a proximal wound-facing face and a distal face, the transmission layer positioned over the distal face of the wound contact layer.

16. The wound dressing apparatus of claim 15, wherein the at least one absorbent layer comprises:
- a first absorbent layer comprising a proximal wound-facing face and a distal face, the first absorbent layer positioned on the distal face of the transmission layer; and
- a second absorbent layer comprising a proximal wound-facing face and a distal face, the second absorbent layer positioned on the distal face of the first absorbent layer.

* * * * *